(12) United States Patent
Roth et al.

(10) Patent No.: US 7,959,899 B2
(45) Date of Patent: Jun. 14, 2011

(54) MOLECULAR SIEVE COMPOSITION (EMM-10-P), ITS METHOD OF MAKING, AND USE FOR HYDROCARBON CONVERSIONS

(75) Inventors: Wieslaw J. Roth, Sewell, NJ (US); Thomas Yorke, Toms River, NJ (US); Michael C. Kerby, Houston, TX (US); Simon C. Weston, Annandale, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 695 days.

(21) Appl. No.: 11/823,129

(22) Filed: Jun. 27, 2007

(65) Prior Publication Data

US 2008/0027259 A1    Jan. 31, 2008

Related U.S. Application Data

(60) Provisional application No. 60/834,030, filed on Jul. 28, 2006, provisional application No. 60/834,031, filed on Jul. 28, 2006, provisional application No. 60/926,204, filed on Apr. 25, 2007, provisional application No. 60/834,001, filed on Jul. 28, 2006.

(51) Int. Cl.
| | |
|---|---|
| C01B 39/48 | (2006.01) |
| C01B 39/46 | (2006.01) |
| C10G 11/05 | (2006.01) |
| C10G 47/16 | (2006.01) |
| C10G 49/08 | (2006.01) |
| C10G 25/03 | (2006.01) |
| C07C 7/13 | (2006.01) |

(52) U.S. Cl. .................. 423/718; 423/716; 208/111.01; 208/111.15; 208/136; 208/143; 208/310 Z

(58) Field of Classification Search .................. 423/718, 423/716; 208/46, 110.01, 111.15, 136, 143, 208/310 Z
See application file for complete search history.

(56) References Cited

U.S. PATENT DOCUMENTS

| | | | |
|---|---|---|---|
| 4,439,409 | A | 3/1984 | Puppe et al. |
| 4,826,667 | A | 5/1989 | Zones et al. |
| 4,954,325 | A | 9/1990 | Rubin et al. |
| 5,236,575 | A | 8/1993 | Bennett et al. |
| 5,250,277 | A | 10/1993 | Kresge et al. |
| 5,362,697 | A | 11/1994 | Fung et al. |
| 6,077,498 | A | 6/2000 | Diaz Cabañas et al. |
| 6,936,744 | B1 | 8/2005 | Cheng et al. |

FOREIGN PATENT DOCUMENTS

| | | |
|---|---|---|
| DE | 36 25 693 | 2/1988 |
| EP | 0 293 032 | 11/1988 |

(Continued)

OTHER PUBLICATIONS

U.S. Appl. No. 60/834,010, filed Jul. 28, 2006, Lai, et al.

(Continued)

*Primary Examiner* — David M Brunsman
(74) *Attorney, Agent, or Firm* — Darryl M. Tyus; Xiaobing Feng

(57) ABSTRACT

This invention relates to a crystalline molecular sieve having, in its as-synthesized form, an X-ray diffraction pattern including d-spacing maxima at 13.18±0.25 and 12.33±0.23 Angstroms, wherein the peak intensity of the d-spacing maximum at 13.18±0.25 Angstroms is at least as great as 90% of the peak intensity of the d-spacing maximum at 12.33±0.23 Angstroms. This invention also relates to a method of making thereof.

47 Claims, 7 Drawing Sheets

X-ray diffraction pattern of the material prepared according to Example 1.

FOREIGN PATENT DOCUMENTS

| WO | WO 97/17290 | 5/1997 |
| WO | WO 01/21562 | 3/2001 |
| WO | WO 2005/118476 | 12/2005 |
| WO | WO 2006/015824 | 2/2006 |
| WO | WO 2006/015825 | 2/2006 |
| WO | WO 2006/015826 | 2/2006 |
| WO | WO 2006/094006 | 9/2006 |
| WO | WO 2007/094937 | 8/2007 |
| WO | WO 2007/094938 | 8/2007 |

OTHER PUBLICATIONS

U.S. Appl. No. 60/834,032, filed Jul. 28, 2006, Roth, et al.
U.S. Appl. No. 60/834,031, filed Jul. 28, 2006, Roth, et al.
U.S. Appl. No. 60/834,115, filed Jul. 28, 2006, Roth, et al.
U.S. Appl. No. 60/834,030, filed Jul. 28, 2006, Roth, et al.
U.S. Appl. No. 60/834,001, filed Jul. 28, 2006, Roth, et al.
U.S. Appl. No. 60/926,204, filed Apr. 25, 2007, Roth, et al.
S. H. Lee, et al., *Chemistry Letters*, vol. 32, No. 6, pp. 542-543 (2003).
S. H. Lee, et al., "Reinvestigation into the synthesis of zeolites using diquaternary alkylammonium ions $(CH_3)_3N^{+}(CH_2)_nN^{+}(CH_3)_3$ with n=3-10 as structure-directing agents", *Microporous and Mesoporous Materials*, vol. 68, pp. 97-104 (2004).
W. Roth, et al., "MCM-22 zeolite family and the delaminated zeolite MCM-56 obtained in one-step synthesis", *Studies in Surface Science Catalysis*, vol. 158, p. 19 (2005).
Lok et al., "*The Role of Organic Molecules in Molecular Sieve Synthesis*," Zeolites, vol. 8 (October), pp. 282-291 (1983).

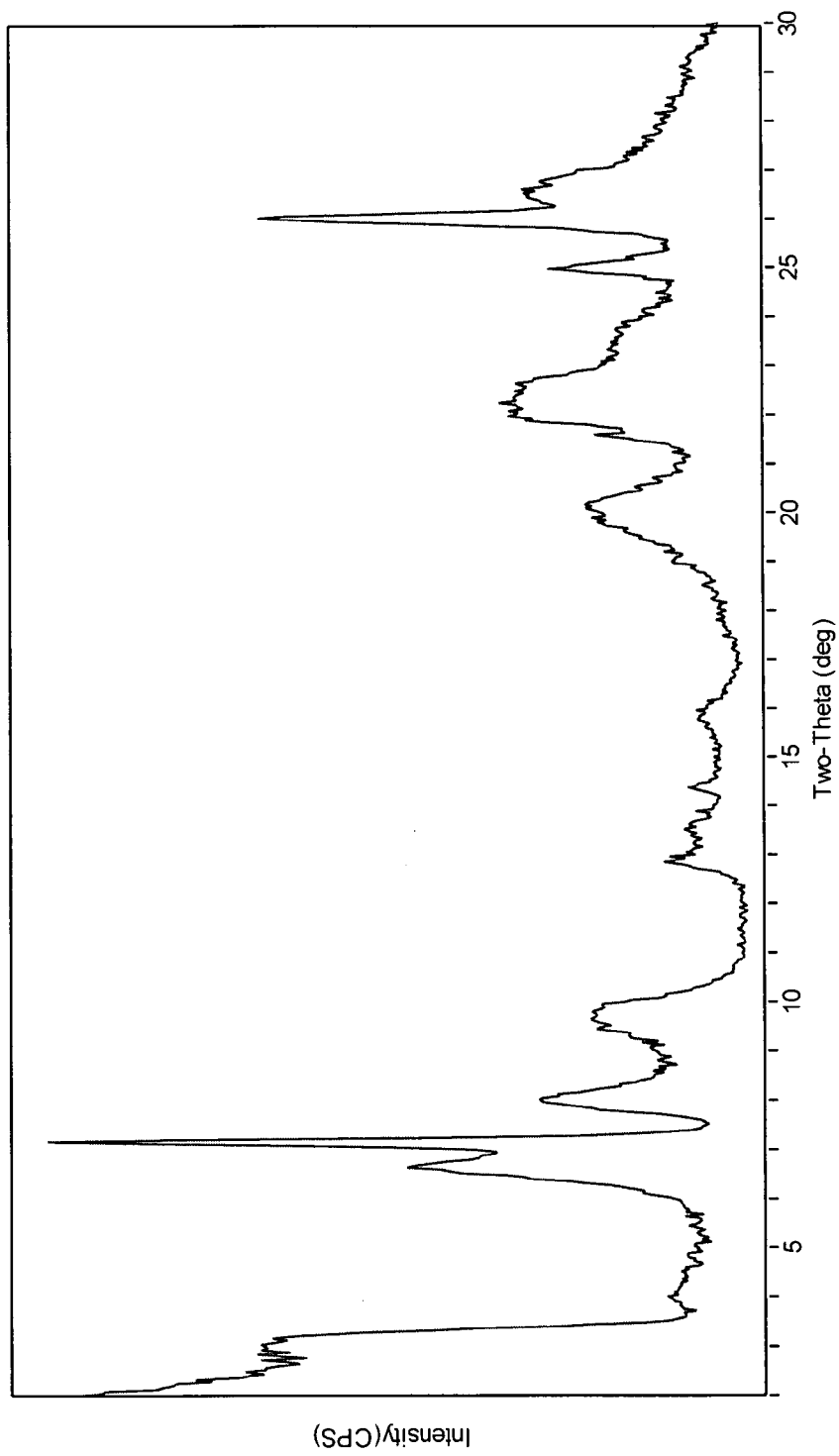
Figure 1. X-ray diffraction pattern of the material prepared according to Example A.

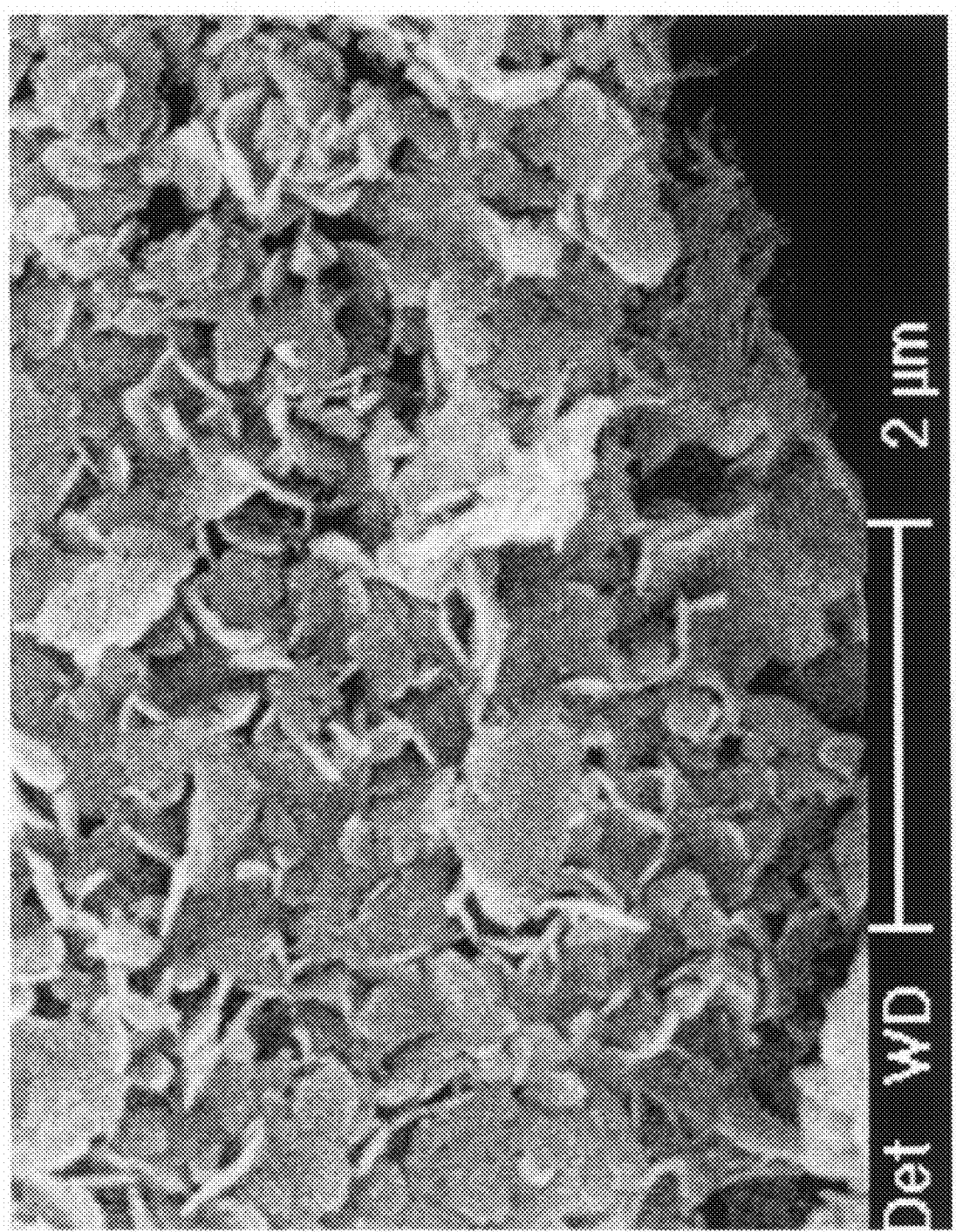
Figure 2. SEM of the material prepared according to Example A

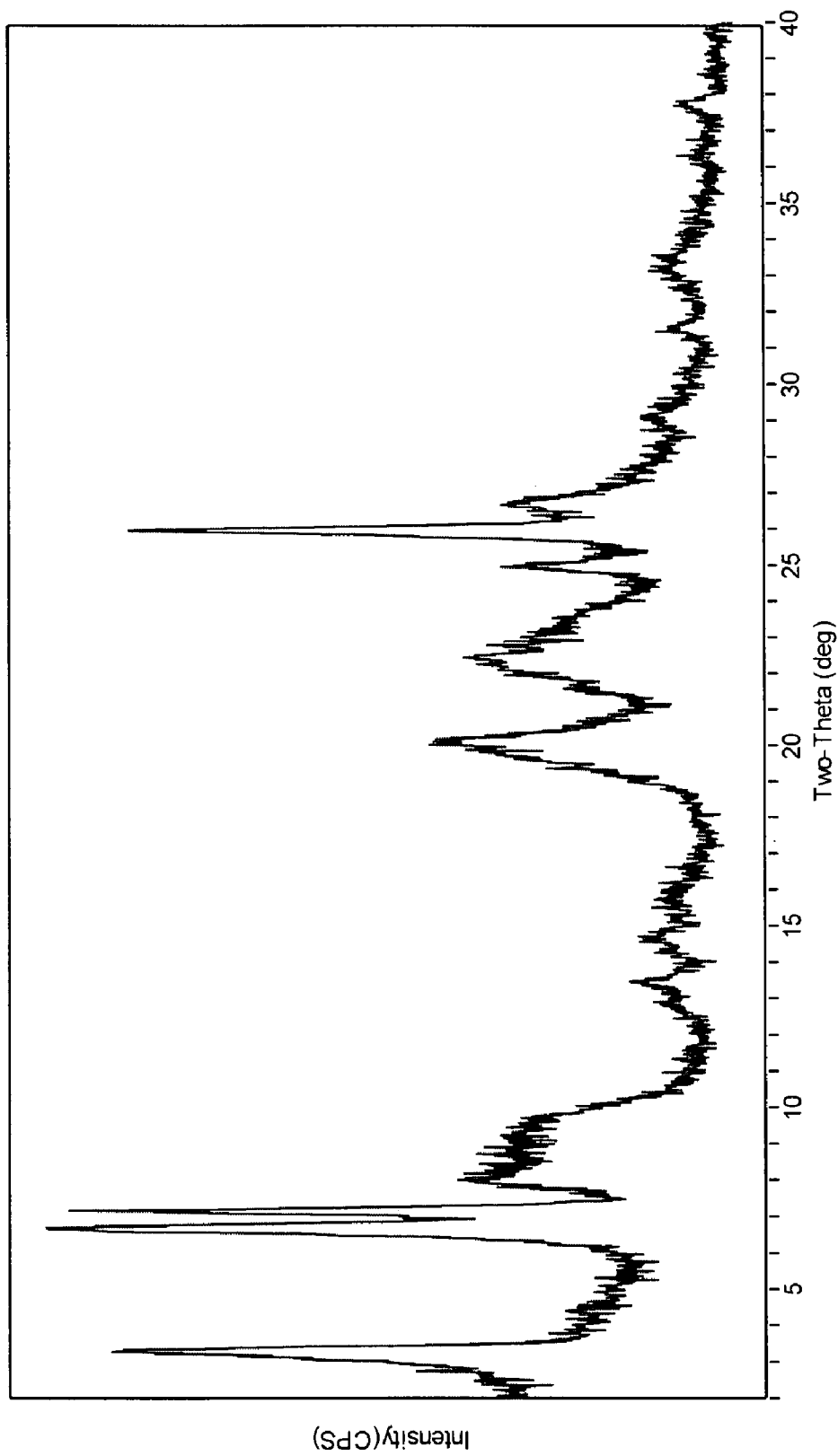
Figure 3. X-ray diffraction pattern of the material prepared according to Example 1.

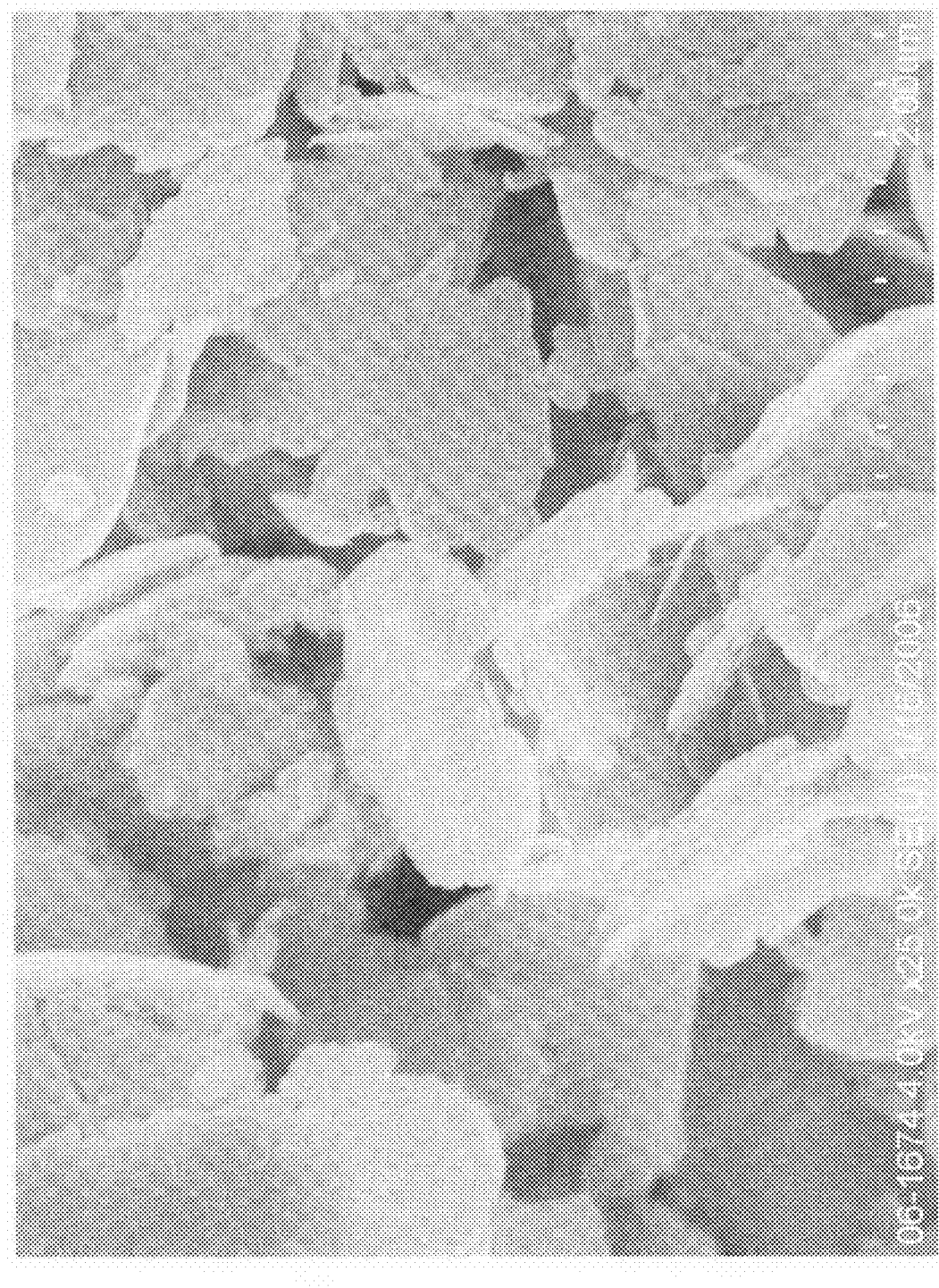
Figure 4. SEM of the material prepared according to Example 1.

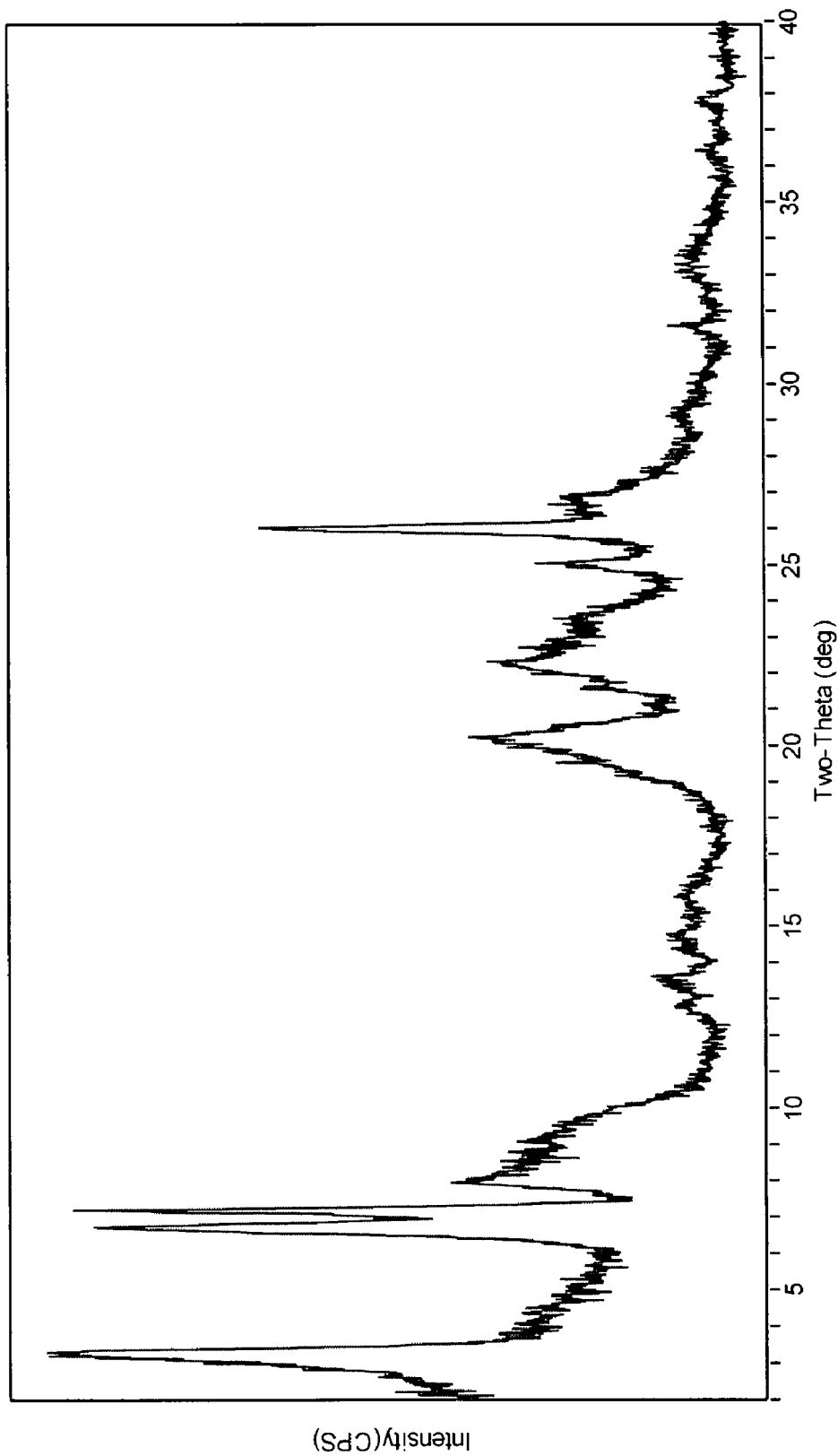
Figure 5. X-ray diffraction pattern of the material prepared according to Example 2

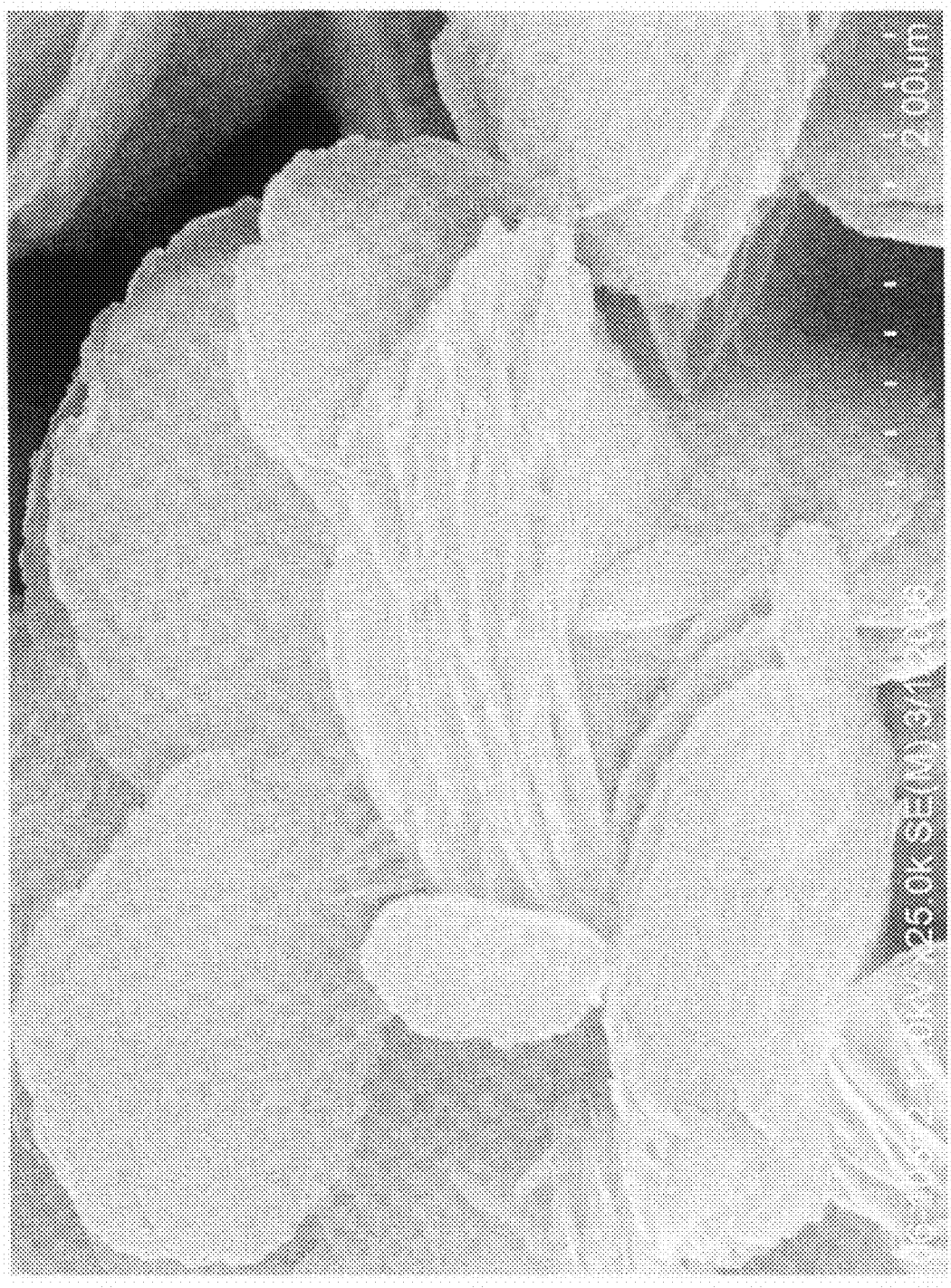
Figure 6. SEM of the material prepared according to Example 2

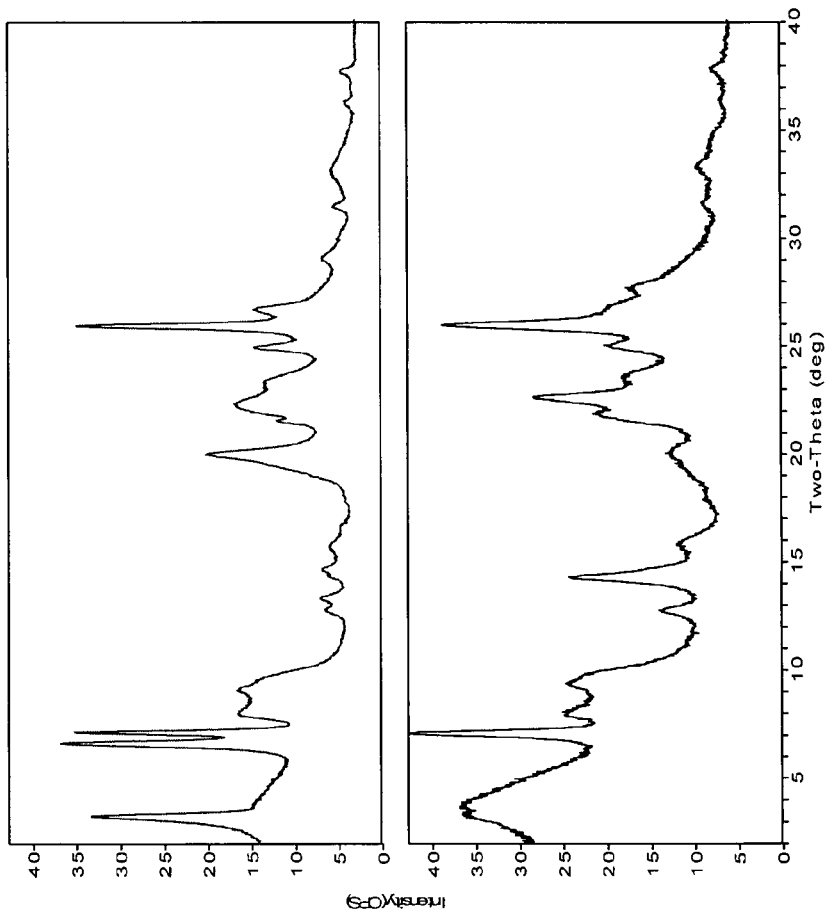
Figure 7. X-ray diffraction pattern of the materials prepared according to Example 5: as-synthesized (top), ammonium exchanged and calcined sample (bottom).

MOLECULAR SIEVE COMPOSITION (EMM-10-P), ITS METHOD OF MAKING, AND USE FOR HYDROCARBON CONVERSIONS

CROSS-REFERENCE TO RELATED APPLICATIONS

This application claims benefit of U.S. Provisional Patent Application No. 60/834,030, filed Jul. 28, 2006, U.S. Provisional Patent Application No. 60/834,001, filed Jul. 28, 2006, U.S. Provisional Patent Application No. 60/834,031, filed Jul. 28, 2006, and U.S. Provisional Patent Application No. 60/926,204, filed Apr. 25, 2007, the references of which are herein incorporated.

FIELD

This invention relates to a novel molecular sieve composition (EMM-10-P), a method of making thereof and the use thereof for hydrocarbon conversions. In particular, this invention relates to a novel MCM-22 family molecular sieve composition, a method of making thereof and the use thereof for hydrocarbon conversions.

BACKGROUND OF THIS DISCLOSURE

Molecular sieve materials, both natural and synthetic, have been demonstrated in the past to have catalytic properties for various types of hydrocarbon conversion. Certain molecular sieves, zeolites, AlPOs, mesoporous materials, are ordered, porous crystalline materials having a definite crystalline structure as determined by X-ray diffraction (XRD). Within the crystalline molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Such molecular sieves, both natural and synthetic, include a wide variety of positive ion-containing crystalline silicates. These silicates can be described as rigid three-dimensional framework of $SiO_4$ and Periodic Table Group 13 element oxide (e.g., $AlO_4$). The tetrahedra are cross-linked by the sharing of oxygen atoms whereby the ratio of the total Group 13 element (e.g., aluminum) and silicon atoms to oxygen atoms is 1:2. The electrovalence of the tetrahedra containing the Group 13 element (e.g., aluminum) is balanced by the inclusion in the crystal of a cation, for example a proton, an alkali metal or an alkaline earth metal cation. This can be expressed wherein the ratio of the Group 13 element (e.g., aluminum) to the number of various cations, such as $H^+$, $Ca^{2+}/2$, $Sr^{2+}/2$, $Na^+$, $K^+$, or $Li^+$, is equal to unity.

Molecular sieves that find application in catalysis include any of the naturally occurring or synthetic crystalline molecular sieves. Examples of these zeolites include large pore zeolites, intermediate pore size zeolites, and small pore zeolites. These zeolites and their isotypes are described in "Atlas of Zeolite Framework Types", eds. W. H. Meier, D. H. Olson and Ch. Baerlocher, Elsevier, Fifth Edition, 2001, which is hereby incorporated by reference. A large pore zeolite generally has a pore size of at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite hasp a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, chabazite, zeolite T, gmelinite, ALPO-17, and clinoptilolite.

U.S. Pat. No. 4,439,409 refers to a crystalline molecular sieve composition of matter named PSH-3 and its synthesis from a hydrothermal reaction mixture containing hexamethyleneimine, an organic compound which acts as directing agent for synthesis of the MCM-56 (U.S. Pat. No. 5,362,697). Hexamethyleneimine is also taught for use in synthesis of crystalline molecular sieves MCM-22 (U.S. Pat. No. 4,954,325) and MCM-49 (U.S. Pat. No. 5,236,575). A molecular sieve composition of matter referred to as zeolite SSZ-25 (U.S. Pat. No. 4,826,667) is synthesized from a hydrothermal reaction mixture containing an adamantane quaternary ammonium ion. U.S. Pat. No. 6,077,498 refers to a crystalline molecular sieve composition of matter named ITQ-1 and its synthesis from a hydrothermal reaction mixture containing one or a plurality of organic additives.

The term "MCM-22 family material" (or "material of the MCM-22 family" or "molecular sieve of the MCM-22 family"), as used herein, includes:

(i) molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth edition, 2001, the entire content of which is incorporated as reference;

(ii) molecular sieves made from a common second degree building block, a 2-dimensional tiling of such MWW framework type unit cells, forming a "monolayer of one unit cell thickness", preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, or any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575) and MCM-56 (described in U.S. Pat. No. 5,362,697). The entire contents of the patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of the molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstroms.

Chem. Lett. Vol. 32, No. 6, page 542-543 (2003) by S. H. Lee, C. H. Shin, and S. B Hong and Microporous and Mesoporous Materials, Vol. 68, page 97-104 (2004) by S. H. Lee, C. H. Shin, D. K. Yang, S. D. Ahn, I. S. Nam and S. B Hong reported a MCM-22 molecular sieve synthesized by crystallizing hydrothermal reaction mixtures prepared from water, $Me_6$-diquat-5 dibromide, Ludox HS-40, aluminum nitrate non-hydrate, and 50 wt % sodium hydroxide solution. The mixtures had a molar composition as shown in Table I. The mixtures were crystallized under crystallization conditions (as shown in Table I) and characterized as pure phase MCM-22 with a crystal size of about 0.5×0.05 μm (micro plates morphology).

TABLE I

| | Chem. Lett. Vol. 32, No. 6, page 542-543 (2003) | Microporous and Mesoporous Materials, Vol. 68, page 97-104 (2004) | |
|---|---|---|---|
| Molar composition of the mixture | | | |
| $SiO_2/Al_2O_3$ | 60 | 30 | 60 |
| $H_2O/SiO_2$ | 40 | 40 | 40 |
| $OH^-/SiO_2$* | 0.63 | 0.4 | 0.5 |
| $OH^-/SiO_2$** | 0.73 | 0.6 | 0.6 |
| $Na^+/SiO_2$ | 0.73 | 0.6 | 0.6 |
| $R/SiO_2$ | 0.15 | 0.1 | 0.1 |
| Crystallization conditions | | | |
| Temperature (° C.) | | 160 | |
| Stirring speed (RPM) | | 100 | |
| Time (hr) | | 168 | |
| Product Characterization | | | |
| XRD Result | | Pure Phase MCM-22 | |
| $SiO_2/Al_2O_3$ (molar ratio) | | 38 | |
| BET area (m²/g) | | 438 | |
| Crystal size | | 0.5 × 0.05 μm | |
| Morphology | | Platelet | Platelet |

*The $OH^-/SiO_2$ of this row is calculated with correction of aluminum source, wherein $Al(NO_3)_3$ was used in both papers.
**The $OH^-/SiO_2$ of this row is calculated without correction of aluminum source.

It is known that crystal morphology, size and aggregation/agglomeration can affect catalyst behavior, especially regarding catalyst activity and stability. There is, therefore, a need for novel crystalline molecular sieve compositions and method of making such novel crystalline molecular sieve compositions, especially molecular sieves of different morphology.

SUMMARY OF THIS DISCLOSURE

This disclosure relates to a crystalline molecular sieve, in its as-synthesized form, identified as EMM-10-P. This disclosure also relates to a method of making EMM-10-P. In some preferred embodiments, the EMM-10-P is an MCM-22 family molecular sieve.

In some embodiments, this disclosure relates to a crystalline molecular sieve having, in its as-synthesized form, an X-ray diffraction pattern including d-spacing maxima at 13.18±0.25 and 12.33±0.23 Angstroms, wherein the peak intensity of the d-spacing maximum at 13.18±0.25 Angstroms is at least as great as 90% of the peak intensity of the d-spacing maximum at 12.33±0.23 Angstroms.

In additional embodiments of this disclosure, the X-ray diffraction pattern of the crystalline molecular sieve further includes two XRD distinguishable peaks with d-spacing maxima at 11.06±0.18 and 9.25±0.13 Angstroms, wherein the peak intensity of the d-spacing maximum at 11.06±0.18 Angstroms is at least as great as the peak intensity of the d-spacing maximum at 9.25±0.13 Angstroms. Additionally, the peaks with d-spacing maxima at 11.06±0.18 and 9.25±0.13 Angstroms may be non-discrete peaks.

In yet more embodiments, this disclosure relates to a crystalline MCM-22 family molecular sieve that has a total surface area of greater than 450 m²/g as measured by the $N_2$ BET method. The crystalline MCM-22 family molecular sieve preferably has a ratio of the external surface area over the total surface area of less than 0.15 after conversion into H-form by exchange with ammonium nitrate and calcination, wherein the external surface area is determined from a t-plot of the $N_2$ BET.

In yet some additional embodiments, this disclosure relates to a crystalline molecular sieve that has a morphology of tabular habit, wherein at least 50 wt % of the crystalline molecular sieve have a crystal diameter greater than 1 μm as measured by the SEM, preferably greater than 2 μm as measured by the SEM.

In some aspects, the crystalline molecular sieve has a morphology of tabular habit, wherein at least 50 wt % of the crystalline molecular sieve have a crystal thickness of about 0.025 μm as measured by the SEM.

In one aspect, the crystalline molecular sieve of this disclosure is an MCM-22 family molecular sieve.

In some embodiments, this disclosure relates to a method of making a crystalline molecular sieve, the method comprising the steps of:

(a) providing a mixture comprising at least one source of at least one tetravalent element (Y), at least one source of at least one alkali or alkali earth metal element, at least one directing-agent (R), water, and optionally at least one source of at least one trivalent element (X), said mixture having the following molar ratio:
  $Y:X_2$=10 to infinity, preferably 10 to 10000, more preferably from 10 to 55;
  $H_2O:Y$=1 to 10000, preferably 1 to 5000, more preferably from 5 to 35;
  $OH^-:Y$ without trivalent element source correction=0.001 to 0.59, and/or $OH^-:Y$ (with trivalent element source correction)=0.001 to 0.39
  $M^+:Y$=0.001 to 2, preferably from 0.1 to 1;
  $R:Y$=0.001 to 2, preferably from 0.1 to 1;
  wherein M is an alkali metal and R is at least one N,N,N,N'N'N'-hexamethyl-1,5-pentanediaminium salt ($Me_6$-diquat-5 salt(s)), preferably R is selected from the group consisting of $Me_6$-diquat-5 dibromide, $Me_6$-diquat-5 dichloride, $Me_6$-diquat-5 difluoride, $Me_6$-diquat-5 diiodide, $Me_6$-diquat-5 dihydroxide, $Me_6$-diquat-5 sulfate, $Me_6$-diquat-5 dinitrate, $Me_6$-diquat-5 hydroxide bromide, $Me_6$-diquat-5 hydroxide chloride, $Me_6$-diquat-5 hydroxide fluoride, $Me_6$-diquat-5 hydroxide iodide, $Me_6$-diquat-5 hydroxide nitrate, $Me_6$-diquat-5 fluoride bromide, $Me_6$-diquat-5 fluoride chloride, $Me_6$-diquat-5 fluoride iodide, $Me_6$-diquat-5 fluoride nitrate, $Me_6$-diquat-5 chloride bromide, $Me_6$-diquat-5 chloride iodide, $Me_6$-diquat-5 chloride nitrate, $Me_6$-diquat-5 iodide bromide, $Me_6$-diquat-5 bromide nitrate, and any mixtures thereof, more preferably R is selected from the group consisting of $Me_6$-diquat-5 dibromide, $Me_6$-diquat-5 dichloride, $Me_6$-diquat-5 difluoride, $Me_6$-diquat-5 diiodide, $Me_6$-diquat-5 dihydroxide, $Me_6$-diquat-5 sulfate, $Me_6$-diquat-5 dinitrate, and any mixtures thereof, most preferably R is $Me_6$-diquat-5 dibromide; and (b) submitting the mixture at crystallization conditions to form a product comprising the desired crystalline molecular sieve, wherein the crystallization conditions comprise a temperature in the range of from 100° C. to 200° C., preferably from about 140 to about 180C.; and a crystallization time from about 1 hour to 400 hours, preferably from about 1 to 200 hours, optionally a stirring speed in the range of from 0 to 1000 RPM, preferably from 0 to 400 RPM.

In additional embodiments, this disclosure relates to a method of manufacturing a crystalline molecular sieve, the method comprising the steps of:

(a) providing a mixture comprising at least one source of at least one tetravalent element (Y), at least one source of at least one alkali or alkali earth metal element, at least one directing-agent (R), water, and optionally at least one source of at least one trivalent element (X), said mixture having the following molar ratio:
  $Y:X_2$=10 to infinity, preferably 10 to 10000, more preferably from 10 to 55;
  $H_2O:Y$=1 to 10000, preferably 1 to 5000, more preferably from 5 to 35;
  $OH^-:Y$ without trivalent element source correction=0.74 to 2 and/or $OH^-:Y$ with trivalent element source correction=0.64 to 2
  $M^+:Y$=0.001 to 2, preferably from 0.1 to 1;
  $R:Y$=0.001 to 2, preferably from 0.1 to 1;
  wherein M is an alkali metal and R is at least one N,N,N,N'N'N'-hexamethyl-1,5-pentanediaminium salt ($Me_6$-diquat-5 salt(s)), preferably R is selected from the group consisting of $Me_6$-diquat-5 dibromide, $Me_6$-diquat-5 dichloride, $Me_6$-diquat-5 difluoride, $Me_6$-diquat-5 diiodide, $Me_6$-diquat-5 dihydroxide, $Me_6$-diquat-5 sulfate, $Me_6$-diquat-5 dinitrate, $Me_6$-diquat-5 hydroxide bromide, $Me_6$-diquat-5 hydroxide chloride, $Me_6$-diquat-5 hydroxide fluoride, $Me_6$-diquat-5 hydroxide iodide, $Me_6$-diquat-5 hydroxide nitrate, $Me_6$-diquat-5 fluoride bromide, $Me_6$-diquat-5 fluoride chloride, $Me_6$-diquat-5 fluoride iodide, $Me_6$-diquat-5 fluoride nitrate, $Me_6$-diquat-5 chloride bromide, $Me_6$-diquat-5 chloride iodide, $Me_6$-diquat-5 chloride nitrate, $Me_6$-diquat-5 iodide bromide, $Me_6$-diquat-5 bromide nitrate, and any mixtures thereof, more preferably R is selected from the group consisting of $Me_6$-diquat-5 dibromide, $Me_6$-diquat-5 dichloride, $Me_6$-diquat-5 difluoride, $Me_6$-diquat-5 diiodide, $Me_6$-diquat-5 dihydroxide, $Me_6$-diquat-5 sulfate, $Me_6$-diquat-5 dinitrate, and any mixtures thereof, most preferably R is $Me_6$-diquat-5 dibromide;

(b) submitting the mixture at crystallization conditions to form a product comprising the desired crystalline molecular sieve, wherein the crystallization conditions comprise a temperature in the range of from 100° C. to 200° C., preferably from about 140 to about 180C.; and a crystallization time from about 1 hour to 400 hours, preferably from about 1 to 200 hours, optionally a stirring speed in the range of from 0 to 1000 RPM, preferably from 0 to 400 RPM; and (c) recovering the crystalline molecular sieve.

In yet additional embodiments, this disclosure relates to a method of manufacturing a crystalline molecular sieve, the method comprising the steps of:

(a) providing a mixture comprising at least one source of at least one tetravalent element (Y), at least one source of at least one alkali or alkali earth metal element, at least one directing-agent (R), water, and optionally at least one source of at least one trivalent element (X), said mixture having the following molar ratio:
  $Y:X_2$=10 to infinity, preferably 10 to 10000, more preferably from about 10 to 55;
  $H_2O:Y$=1 to 10000, preferably 1 to 5000, more preferably from 5 to 35;
  $OH^-:Y$ without trivalent element source correction=0.61 to 0.72 and/or $OH^-:Y$ with trivalent element source correction=0.41 to 0.49 or 0.51 to 0.62
  $M^+:Y$=0.001 to 2, preferably from 0.1 to 1;
  $R:Y$=0.001 to 2, preferably from 0.1 to 1;
  wherein M is an alkali metal and R is at least one N,N,N,N'N'N'-hexamethyl-1,5-pentanediaminium salt ($Me_6$-diquat-5 salt(s)), preferably R is selected from the group consisting of $Me_6$-diquat-5 dibromide, $Me_6$-diquat-5 dichloride, $Me_6$-diquat-5 difluoride, $Me_6$-diquat-5 diiodide, Me₆-diquat-5 dihydroxide, Me₆-diquat-5 sulfate, Me₆-diquat-5 dinitrate, Me₆-diquat-5 hydroxide bromide, Me₆-diquat-5 hydroxide chloride, Me₆-diquat-5 hydroxide fluoride, Me₆-diquat-5 hydroxide iodide, Me₆-diquat-5 hydroxide nitrate, Me₆-diquat-5 fluoride bromide, Me₆-diquat-5 fluoride chloride, Me₆-diquat-5 fluoride iodide, Me₆-diquat-5 fluoride nitrate, Me₆-diquat-5 chloride bromide, Me₆-diquat-5 chloride iodide, Me₆-diquat-5 chloride nitrate, Me₆-diquat-5 iodide bromide, Me₆-diquat-5 bromide nitrate, and any mixtures thereof, more preferably R is selected from the group consisting of Me₆-diquat-5 dibromide, Me₆-diquat-5 dichloride, Me₆-diquat-5 difluoride, Me₆-diquat-5 diiodide, Me₆-diquat-5 dihydroxide, Me₆-diquat-5 sulfate, Me₆-diquat-5 dinitrate, and any mixtures thereof, most preferably R is Me₆-diquat-5 dibromide;

(b) submitting the mixture at crystallization conditions to form a product comprising the desired crystalline molecular sieve, wherein the crystallization conditions comprise a temperature in the range of from 100° C. to 200° C., preferably from about 140 to about 180C.; and a crystallization time from about 1 hour to 400 hours, preferably from about 1 to 200 hours, optionally a stirring speed in the range of from 0 to 1000 RPM, preferably from 0 to 400 RPM; and (c) recovering the crystalline molecular sieve.

In further additional embodiments, this disclosure relates to a method of manufacturing a crystalline molecular sieve, the method comprising the steps of:

(a) providing a mixture comprising at least one source of at least one tetravalent element (Y), at least one source of at least one alkali or alkali earth metal element, at least one directing-agent (R), water, and optionally at least one source of at least one trivalent element (X), said mixture having the following molar ratio:

Y:X₂=10 to infinity, preferably 10 to 10000, more preferably from 10 to 55;
H₂O:Y=1 to 35, preferably from 5 to 35;
OH⁻:Y=0.001 to 2, preferably from 0.01 to 0.5;
M⁺:Y=0.001 to 2, preferably from 0.1 to 1;
R:Y=0.001 to 2, preferably from 0.1 to 1;

wherein M is an alkali metal and R is at least one N,N,N',N'N'N'-hexamethyl-1,5-pentanediaminium salt (Me₆-diquat-5 salt(s)), preferably R is selected from the group consisting of Me₆-diquat-5 dibromide, Me₆-diquat-5 dichloride, Me₆-diquat-5 difluoride, Me₆-diquat-5 diiodide, Me₆-diquat-5 dihydroxide, Me₆-diquat-5 sulfate, Me₆-diquat-5 dinitrate, Me₆-diquat-5 hydroxide bromide, Me₆-diquat-5 hydroxide chloride, Me₆-diquat-5 hydroxide fluoride, Me₆-diquat-5 hydroxide iodide, Me₆-diquat-5 hydroxide nitrate, Me₆-diquat-5 fluoride bromide, Me₆-diquat-5 fluoride chloride, Me₆-diquat-5 fluoride iodide, Me₆-diquat-5 fluoride nitrate, Me₆-diquat-5 chloride bromide, Me₆-diquat-5 chloride iodide, Me₆-diquat-5 chloride nitrate, Me₆-diquat-5 iodide bromide, Me₆-diquat-5 bromide nitrate, and any mixtures thereof, more preferably R is selected from the group consisting of Me₆-diquat-5 dibromide, Me₆-diquat-5 dichloride, Me₆-diquat-5 difluoride, Me₆-diquat-5 diiodide, Me₆-diquat-5 dihydroxide, Me₆-diquat-5 sulfate, Me₆-diquat-5 dinitrate, and any mixtures thereof, most preferably R is Me₆-diquat-5 dibromide, wherein said OH⁻:Y is calculated with or without trivalent element source correction;

(b) submitting the mixture at crystallization conditions to form a product comprising the desired crystalline molecular sieve, wherein the crystallization conditions comprise a temperature in the range of from 100° C. to 200° C., preferably from about 140 to about 180C.; and a crystallization time from about 1 hour to 400 hours, preferably from about 1 to 200 hours, optionally a stirring speed in the range of from 0 to 1000 RPM, preferably from 0 to 400 RPM; and (c) recovering the crystalline molecular sieve.

In some embodiments, this disclosure relates to a method of manufacturing the crystalline molecular sieve of this disclosure, the method comprising the steps of:

(a) combining at least one silicon source, at least one source of at least one alkali or alkali earth metal element, at least one directing-agent (R), water, and optionally at least one aluminum source, to form a mixture having the following mole composition:

Si:Al₂=10 to infinity; preferably 10 to 10000
H₂O:Si=1 to 10000; preferably 1 to 5000
OH⁻:Si without trivalent element source correction=0.001 to 0.59, and/or OH⁻:Si (with trivalent element source correction)=0.001 to 0.39
M⁺:Si=0.001 to 2
R:Si=0.001 to 0.34 wherein M is an alkali metal and R is at least one N,N,N'N'N'-hexamethyl-1,5-pentanediaminium salt;

(b) treating the mixture at crystallization conditions to form a product comprising the desired crystalline molecular sieve, wherein the crystallization conditions comprise a temperature in the range of from 100° C. to 200° C., and a crystallization time from about 1 hour to 200 hours; and (c) recovering the molecular sieve.

In some aspects, the H2O:Si molar ratio is in the range of from 5 to 35.

Additionally, this disclosure relates to a process for hydrocarbon conversion, comprising the step of:

(a) contacting a hydrocarbon feedstock with the crystalline molecular sieve of this disclosure or manufactured by the method of this disclosure, under conversion conditions to form a conversion product.

These and other facets of the present invention shall become apparent from the following detailed description, Figures, and appended claims.

DESCRIPTION OF THE FIGURES

FIG. 1 shows the X-ray diffraction patterns of the as-synthesized MCM-22 family molecular sieve products of Example A.

FIG. 2 shows the SEM image of the as-synthesized MCM-22 family molecular sieve product of Example A FIG. 3 shows the X-ray diffraction patterns of the as-synthesized MCM-22 family molecular sieve products of Example 1.

FIG. 4 shows the SEM image of the as-synthesized MCM-22 family molecular sieve product of Example 1.

FIG. 5 shows the X-ray diffraction patterns of the as-synthesized MCM-22 family molecular sieve products of Example 2.

FIG. 6 shows the SEM image of the as-synthesized MCM-22 family molecular sieve product of Example 2.

FIG. 7 shows the X-ray diffraction patterns of the as-synthesized (top) and the ammonium exchanged and/or calcined MCM-22 family molecular sieve product(s) (bottom) of Example 4.

DETAILED DESCRIPTION OF THIS DISCLOSURE

Introduction

All patents, patent applications, test procedures, priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The term "tabular habit" morphology as used herein means a tabular mineral having "parallel stacked thin platelike crystals." The term "platelet" morphology as used herein means thin platelike crystals.

It will be understood by a person skilled in the art that the MCM-22 family material may contain impurities, such as amorphous materials; unit cells having non-MWW framework topologies (e.g., MFI, MTW); and/or other impurities (e.g., heavy metals and/or organic hydrocarbons). Typical examples of the non-MCM-22 family molecular sieve(s) co-existing with the MCM-22 family molecular sieve(s) of this disclosure are Kenyaite, EU-1, ZSM-50, ZSM-12, ZSM-48, ZSM-5, Ferrierite, Mordenite, Sodalite, and/or Analcine. Other examples of the non-MCM-22 family molecular sieve(s) co-existing with the MCM-22 family molecular sieve(s) of this disclosure are molecular sieves having framework type of EUO, MTW, FER, MOR, SOD, ANA, and/or MFI. The MCM-22 family materials of this disclosure are preferably substantially free of non-MCM-22 family material(s). The term "substantially free of non-MCM-22 family material(s)" used herein means the MCM-22 family material of this disclosure preferably contains a minor proportion (less than 50 wt %), preferably less than 20 wt %, of non-MCM-22 family materials ("impurities") in the MCM-22 family materials, which weight percent (wt %) values are based on the combined weight of impurities and pure phase MCM-22 family materials.

The MCM-22 crystalline material has a composition involving the molar relationship:

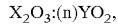

$$X_2O_3{:}(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, the material typically has a formula, on an anhydrous basis and in terms of moles of oxides per n moles of $YO_2$, as follows:

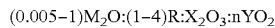

$$(0.005-1)M_2O{:}(1-4)R{:}X_2O_3{:}nYO_2$$

wherein M is an alkali or alkaline earth metal, and R is an organic moiety. The M and R components are associated with the material as a result of their presence during synthesis, and are typically removed by post-synthesis methods well known to those skilled in the art and/or hereinafter more particularly described.

It is to be understood that throughout this detailed description, common characterization techniques were used to describe molecular sieve materials. These common techniques are included ascertaining:
(a) structure and the degree of crystallinity of the molecular sieve material by X-Ray Diffraction (XRD); and/or
(b) morphology and crystal size of the molecular sieve material measured by the Scanning Electron Microscope (SEM); and/or
(c) chemical composition by atomic absorption spectrometry and/or Inductively Coupled Plasma Mass Spectrometry (ICP-MS or ICPMS);
(d) adsorption capacities and surface area measured by nitrogen BET method; and/or
(e) catalytic activities and catalytic stabilities measured by the probing reactions.

X-Ray Powder Diffraction Pattern

The MCM-22 crystalline materials may be distinguished from other crystalline materials by the X-ray diffraction pattern.

The interplanar spacings, d's, were calculated in Angstrom units (Å), and the relative intensities of the lines, $I/I_o$, where the intensity of the strongest line above background, $I_o$, is counted as 100, were derived with the use of a profile fitting routine (or second derivative algorithm). The intensities are uncorrected for Lorentz and polarization effects. The relative intensities are given in terms of the symbols VS=very strong (greater than 60 to 100), S=strong (greater than 40 to 60), M=medium (greater than 20 to 40) and W=weak (0 to 20). It should be understood that diffraction data listed as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-22 with similar materials, e.g., MCM-49, MCM-56, and PSH-3.

The interplanar spacings, d's, were considered broad if they exhibited peak width of about 1.5° or more at half height determined as 50% intensity value from the maximum to the baseline.

The term "XRD distinguishable peak" as used herein is defined as XRD peak with clearly defined peak maximum, which is at least two times of the average background noise level.

The term "non-discrete" peaks (also "unresolved" peaks) in XRD as used herein means peaks having a monotonic profile in-between them (successive points either consistently increasing (or staying even) or decreasing (or staying even) within noise).

The term "discrete" peaks (also "resolved" peaks) in XRD as used herein means XRD peak(s) which are not non-discrete (unresolved).

It should be understood that this X-ray diffraction pattern is characteristic of all the species of the present crystalline composition. The sodium form as well as other cationic forms reveal substantially the same pattern with some minor shifts in interplanar spacing and variation in relative intensity. Other minor variations can occur, depending on the Y to X, e.g., silicon to aluminum, ratio of the particular sample, as well as its degree of thermal treatment (e.g., calcination).

The crystalline molecular sieve composition of this disclosure may be characterized by an X-ray diffraction pattern of the as-synthesized crystalline molecular sieve including d-spacing maxima at 13.18±0.25 and 12.33±0.23 Angstroms (Table II),

TABLE II

| Interplanar d-Spacing (Å) | Relative Intensity, $I/I_o \times 100$ |
|---|---|
| 13.18 ± 0.25 | M-VS |
| 12.33 ± 0.23 | M-VS | wherein the peak intensity of the d-spacing maximum at 13.18±0.25 Angstroms is at least as great as 90% of, preferably at least as great as 100%, more preferably at least as great as 110% of, the peak intensity of the d-spacing maximum at 12.33±0.23 Angstroms.

The crystalline molecular sieve composition of this disclosure may be characterized by an X-ray diffraction pattern of the as-synthesized crystalline molecular sieve further including d-spacing maxima at 11.06±0.18 and 9.25±0.13 Angstroms (Table III),

TABLE III

| Interplanar d-Spacing (Å) | Relative Intensity, $I/I_o \times 100$ |
|---|---|
| 13.18 ± 0.25 | M-VS |
| 12.33 ± 0.23 | M-VS |
| 11.06 ± 0.18 | W-S |
| 9.25 ± 0.13 | W-S | wherein the peak intensity of the d-spacing maximum at 11.06±0.18 Angstroms is at least as great as 90% of, preferably at least as great as 100%, more preferably at least as great as 110% of, the peak intensity of the d-spacing maximum at 9.25±0.13 Angstroms.

The crystalline molecular sieve composition of this disclosure may be characterized further by a feature that the d-spacing maxima at 11.1±0.18 and 9.3±0.13 Angstroms are non-discrete peaks.

The crystalline molecular sieve composition of this disclosure may be characterized by an X-ray diffraction pattern of the as-synthesized crystalline molecular sieve including d-spacing maxima of as-as listed in Table IV or Table V.

TABLE IV

| Interplanar d-Spacing (Å) | Relative Intensity, $I/I_o \times 100$ |
|---|---|
| 13.18 ± 0.25 | M-VS |
| 12.33 ± 0.23 | M-VS |
| 11.06 ± 0.18 | W-S |
| 9.07 ± 0.13 | W-S |
| 3.57 ± 0.06 | W-M |
| 3.43 ± 0.06 | M-VS |

TABLE V

| Interplanar d-Spacing (Å) | Relative Intensity, $I/I_o \times 100$ |
|---|---|
| 13.18 ± 0.25 | M-VS |
| 12.33 ± 0.23 | M-VS |
| 11.06 ± 0.18 | W-S |
| 9.07 ± 0.13 | W-S |
| 6.57 ± 0.15 | W-M |
| 4.41 ± 0.1 | W-M, broad |
| 3.96 ± 0.08 | W-VS, broad |
| 3.57 ± 0.06 | W-M |
| 3.43 ± 0.06 | M-VS |
| 3.34 ± 0.05 | W-S |

Scanning Electron Microscope (SEM)

The SEM image of an MCM-22 molecular sieve produced according to the method of manufacturing of U.S. Pat. No. 4,954,325 is shown in FIG. 2. The MCM-22 molecular sieve according to method of manufacturing of U.S. Pat. No. 4,954,325 has a thin layered less defined hexagonal platelets morphology and an average platelet diameter of less than about 1 µm, determined by the SEM (FIG. 2). The majority of the platelet crystal has an average platelet diameter of less than about 0.5 micron (µm).

The as-synthesized known MCM-22 crystalline material disclosed in Chem. Lett. Vol. 32, No. 6, page 542-543 (2003) by S. H. Lee, C. H. Shin, and S. B Hong is reported as having a particle size of about 0.5×0.05 □µm and a platelet morphology.

The SEM image of a crystalline molecular sieve of this disclosure is shown in FIGS. 4 and 6. The crystalline molecular sieve of this disclosure as shown in (FIGS. 4 and 6) has a crystal morphology of multilayered platelet aggregates with a majority, preferably at least 50 wt %, more preferably at least 75 wt %, of the crystals of the crystalline molecular sieves, having an average platelet diameter greater than 1 □µm. In addition, the crystalline molecular sieve of this disclosure (FIGS. 4 and 6) preferably has a crystal morphology of multilayered platelet aggregates with a majority, preferably at least 50 wt %, more preferably at least 75 wt %, of the crystals of the crystalline molecular sieves, having an average platelet thickness of about 0.025 □µm.

Surface Areas and Adsorption Uptake

The overall surface area of a molecular sieve may be measured by the Brunauer-Emmett-Teller (BET) method using adsorption-desorption of nitrogen (temperature of liquid nitrogen, 77 K). The internal surface area may be calculated using t-plot of the Brunauer-Emmett-Teller (BET) measurement. The external surface area is calculated by subtracting the internal surface area from the overall surface area measured by the Brunauer-Emmett-Teller (BET) measurement.

The crystalline molecular sieve (after calcination) of this disclosure may be characterized by a preferred total surface area (sum of the external and the internal surface areas, as measured by the BET method) of greater than 450 $m^2/g$, preferably greater than 475 $m^2/g$, and more preferably greater than 500 $m^2/g$.

In addition, the crystalline molecular sieve (after calcination) of this disclosure may be characterized by the ratio of the external surface area (as measured by the t-plot of BET method) over the total surface area of preferably less than 0.15, more preferably less than 0.13, or even more preferably less than 0.12.

Formulation of the Hydrothermal Reaction Mixtures

Synthetic molecular sieves are often prepared from aqueous hydrothermal reaction mixtures (synthesis mixture(s) or synthetic gel(s)) comprising sources of appropriate oxides. Organic directing agents may also be included in the hydrothermal reaction mixture for the purpose of influencing the production of a molecular sieve having the desired structure. The use of such directing agents is discussed in an article by Lok et al. entitled "The Role of Organic Molecules in Molecular Sieve Synthesis" appearing in Zeolites, Vol. 3, October, 1983, pp. 282-291.

After the components of the hydrothermal reaction mixture are properly mixed with one another, the hydrothermal reaction mixture is subjected to appropriate crystallization conditions. Such conditions usually involve heating of the hydrothermal reaction mixture to an elevated temperature possibly with stirring. Room temperature aging of the hydrothermal reaction mixture is also desirable in some instances.

After the crystallization of the hydrothermal reaction mixture is complete, the crystalline product may be recovered from the remainder of the hydrothermal reaction mixture, especially the liquid contents thereof. Such recovery may involve filtering the crystals and washing these crystals with water. However, in order to remove the entire undesired residue of the hydrothermal reaction mixture from the crystals, it is often necessary to subject the crystals to a high temperature calcination e.g., at 500° C., possibly in the presence of oxygen. Such a calcination treatment not only removes water from the crystals, but this treatment also serves to decompose and/or oxidize the residue of the organic directing agent which may be occluded in the pores of the crystals, possibly occupying ion exchange sites therein.

The crystalline molecular sieve material of this disclosure may be prepared from a hydrothermal reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, the hydrothermal reaction mixture having a composition, in terms of mole ratios of oxides, within the following ranges:

TABLE VI

| Reactants | Useful | Preferred |
| --- | --- | --- |
| $YO_2/X_2O_3$ | 10 to infinity | 15-55 |
| $H_2O/YO_2$ | 1 to 10000 | 5-35 |
| $OH^-/YO_2$* | 0.001-0.39 | 0.1-0.35 |
| $OH^-/YO_2$** | 0.001-0.59 | 0.1-0.5 |
| $M/YO_2$ | 0.001-2 | 0.1-1 |
| $R/YO_2$ | 0.001-2 | 0.01-0.5 |
| Seed*** | 0-25 wt % | 1-5 wt % |
| R | Me$_6$-diquat-5 salt(s) | Me$_6$-diquat-5 salt(s) |

*The $OH^-/YO_2$ of this row is calculated with correction of trivalent element source.
**The $OH^-/YO_2$ of this row is calculated without correction of trivalent element source.
***The weight percent (wt %) of seed is based on the weight of the solid tetrahedral element oxide.

For these embodiments when reaction mixture for hydrothermal reaction having a composition as disclosed in Table VI, the $OH^-/YO_2$ molar ratio without correction of trivalent element source ranges from about 0.001 to about 0.59 and/or $OH^-/YO_2$ molar ratio with correction of trivalent element source ranges from about 0.001 to about 0.39.

The following $OH^-:YO_2$ molar ratios (without correction of trivalent element source) are useful lower $OH^-:YO_2$ molar ratio (without correction of trivalent element source) limits for these embodiments as disclosed in Table VI: 0.001, 0.002, 0.005, 0.01, 0.02, 0.05, 0.1, 0.2, 0.5, and 0.55. The following $OH^-:YO_2$ molar ratios (without correction of trivalent element source) are useful upper $OH^-:YO_2$ molar ratio (without correction of trivalent element source) limits for these embodiments as disclosed in Table VI: 0.59, 0.55, 0.51, 0.5, 0.4, 0.3, 0.2 and 0.1. The $OH^-:YO_2$ molar ratio (without correction of trivalent element source) ideally falls in a range between any one of the above-mentioned lower limits and any one of the above-mentioned upper limits, so long as the lower limit is less than or equal to the upper limit. The $OH^-:YO_2$ molar ratio (without correction of trivalent element source) may be present in an amount ranging from 0.001 to 0.59 in one embodiment, alternatively 0.01 to 0.5, alternatively 0.1 to 0.5, alternatively and from 0.1 to 0.4 in another embodiment.

The following $OH^-:YO_2$ molar ratios (with correction of trivalent element source) are useful lower $OH^-:YO_2$ molar ratio (with correction of trivalent element source) limits for these embodiments as disclosed in Table VI: 0.001, 0.002, 0.005, 0.01, 0.02, 0.05, 0.1, 0.2, 0.3, and 0.35. The following $OH^-:YO_2$ molar ratios (with correction of trivalent element source) are useful upper $OH^-:YO_2$ molar ratio (with correction of trivalent element source) limits for these embodiments as disclosed in Table VI: 0.39, 0.35, 0.31, 0.3, 0.2 and 0.1. The $OH^-:YO_2$ molar ratio (with correction of trivalent element source) ideally falls in a range between any one of the above-mentioned lower limits and any one of the above-mentioned upper limits, so long as the lower limit is less than or equal to the upper limit. The $OH^-:YO_2$ molar ratio (with correction of trivalent element source) may be present in an amount ranging from 0.001 to 0.39 in one embodiment, alternatively 0.01 to 0.35, alternatively 0.1 to 0.3, alternatively and from 0.1 to 0.25 in another embodiment.

The crystalline molecular sieve material of this disclosure may alternatively be prepared from a hydrothermal reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, the hydrothermal reaction mixture having a composition, in terms of mole ratios of oxides, within the following ranges:

TABLE VII

| Reactants | Useful | Preferred |
| --- | --- | --- |
| $YO_2/X_2O_3$ | 10 to infinity | 15-55 |
| $H_2O/YO_2$ | 1 to 10000 | 5-35 |
| $OH^-/YO_2$* | 0.64-2 | 0.7-2 |
| $OH^-/YO_2$** | 0.74-2 | 0.8-2 |
| $M/YO_2$ | 0.001-2 | 0.1-1 |
| $R/YO_2$ | 0.001-2 | 0.01-0.5 |
| Seed*** | 0-25 wt % | 1-5 wt % |
| R | Me$_6$-diquat-5 salt(s) | Me$_6$-diquat-5 salt(s) |

*The $OH^-/YO_2$ of this row is calculated with correction of trivalent element source.
**The $OH^-/YO_2$ of this row is calculated without correction of trivalent element source.
***The weight percent (wt %) of seed is based on the weight of the solid tetrahedral element oxide.

For these embodiments when reaction mixture for hydrothermal reaction having a composition as disclosed in Table VII, the $OH^-/YO_2$ molar ratio without correction of trivalent element source ranges from about 0.74 to about 2 and/or the $OH^-/YO_2$ molar ratio with correction of trivalent element source ranges from about 0.64 to about 2.

The following OH—/YO2 molar ratios (without correction of trivalent element source) are useful lower OH—/YO2 molar ratio (without correction of trivalent element source) limits for all disclosure processes: 0.74, 0.77, 0.78, 0.80, 0.90, 1 and 1.5. The following OH—/YO2 molar ratios (without correction of trivalent element source) are useful upper OH—/YO2 molar ratio (without correction of trivalent element source) limits for all disclosure processes: 2, 1.6, 1.4, 1.3, 1.2, 1, 0.9 and 0.8. The OH—/YO2 molar ratio (without correction of trivalent element source) ideally falls in a range between any one of the above-mentioned lower limits and any one of the above-mentioned upper limits, so long as the lower limit is less than or equal to the upper limit. The OH—/YO2 molar ratio (without correction of trivalent element source) may be present in an amount ranging from 0.74 to 2 in one embodiment, alternatively 0.8 to 2, alternatively 0.8 to 1, alternatively and from 0.8 to 1.1 in another embodiment.

The following OH—/YO2 molar ratios (with correction of trivalent element source) are useful lower OH—/YO2 molar ratio (with correction of trivalent element source) limits for all disclosure processes: 0.64, 0.65, 0.66, 0.7, 0.75, 0.80, 0.90, 1 and 1.5. The following OH—/YO2 molar ratios (with correction of trivalent element source) are useful upper OH—/YO2 molar ratio (with correction of trivalent element source) limits for all disclosure processes: 2, 1.6, 1.4, 1.3, 1.2, 1, 0.9 and 0.8. The OH—/YO2 molar ratio (with correction of trivalent element source) ideally falls in a range between any one of the above-mentioned lower limits and any one of the above-mentioned upper limits, so long as the lower limit is less than or equal to the upper limit. The OH—/YO2 molar ratio (with correction of trivalent element source) may be present in an amount ranging from 0.74 to 2 in one embodiment, alternatively 0.8 to 2, alternatively 0.8 to 1, alternatively and from 0.8 to 1.1 in another embodiment.

The crystalline molecular sieve material of this disclosure may alternatively be prepared from a hydrothermal reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, the hydrothermal reaction mixture having a composition, in terms of mole ratios of oxides, within the following ranges:

TABLE VIII

| Reactants | Useful | Preferred |
|---|---|---|
| $YO_2/X_2O_3$ | 10 to infinity | 15-55 |
| $H_2O/YO_2$ | 5-35 | 5-30 |
| $OH^-/YO_2$* | 0.001-2 | 0.001-2 |
| $M/YO_2$ | 0.001-2 | 0.1-1 |
| $R/YO_2$ | 0.001-2 | 0.01-0.5 |
| Seed** | 0-25 wt % | 1-5 wt % |
| R | $Me_6$-diquat-5 salt(s) | $Me_6$-diquat-5 salt(s) |

*The $OH^-/YO_2$ of this row is calculated with or without correction of trivalent element source.
**The weight percent (wt %) of seed is based on the weight of the solid tetrahedral element oxide.

The sources of the various elements required in the final product may be any of those in commercial use or described in the literature, as may the method of preparation of the synthesis mixture.

Y is a tetravalent element selected from Groups 4-14 of the Periodic Table of the Elements, such as silicon and/or germanium, preferably silicon. In some embodiments of this disclosure, the source of $YO_2$ comprises solid $YO_2$, preferably about 30 wt % solid $YO_2$ in order to obtain the crystal product of this disclosure. When $YO_2$ is silica, the use of a silica source containing preferably about 30 wt % solid silica, e.g., silica sold by Degussa under the trade names Aerosil or Ultrasil (a precipitated, spray dried silica containing about 90 wt % silica), an aqueous colloidal suspension of silica, for example one sold by Grace Davison under the trade name Ludox, or HiSil (a precipitated hydrated $SiO_2$ containing about 87 wt % silica, about 6 wt % free $H_2O$ and about 4.5 wt % bound $H_2O$ of hydration and having a particle size of about 0.02 micron) favors crystal formation from the above mixture. Preferably, therefore, the $YO_2$, e.g., silica, source contains about 30 wt % solid $YO_2$, e.g., silica, and more preferably about 40 wt % solid $YO_2$, e.g., silica. The source of silicon may also be a silicate, e.g., an alkali metal silicate, or a tetraalkyl orthosilicate.

In additional embodiments of this disclosure, the source of $YO_2$ comprises acid of the tetravalent element (Y). When $YO_2$ is silica, the silica source may be silicic acid.

X is a trivalent element selected from Groups 3-13 of the Periodic Table of the Elements, such as aluminum, and/or boron, and/or iron and/or gallium, preferably aluminum. The source of $X_2O_3$, e.g., aluminum, is preferably aluminum sulphate or hydrated alumina. Other aluminum sources include, for example, other water-soluble aluminum salts, sodium aluminate, or an alkoxide, e.g., aluminum isopropoxide, or aluminum metal, e.g., in the form of chips.

The alkali or alkali earth metal element is advantageously lithium, sodium, potassium, calcium, or magnesium. The source of alkali or alkali earth metal element is advantageously being metal oxide, metal chloride, metal fluoride, metal sulfate, metal nitrate, or metal aluminate. The sodium source advantageously being sodium hydroxide or sodium aluminate. The alkali metal may also be replaced by ammonium ($NH_4^+$) or its equivalents, e.g., alkyl-ammonium ion.

In some embodiments of this disclosure, the $M:YO_2$, e.g., $M:SiO_2$ molar ratio ranges from a low value of 0.001, preferably 0.01, and optionally 0.1, to a high value of 2.0, preferably 1, and optionally 0.5. The $M:YO_2$, e.g., $M:SiO_2$ molar ratio ideally falls in a range comprising any combination of the above-mentioned low value(s) and the above-mentioned high values(s).

In some embodiments of this disclosure, the $H2O:YO_2$, e.g., $H2O:SiO_2$ molar ratio ranges from a low value of 1, preferably 5, and optionally 10, to a high value of 10000, preferably 5000, and optionally 500. The $H2O:YO_2$, e.g., $H2O:SiO_2$ molar ratio ideally falls in a range comprising any combination of the above-mentioned low value(s) and the above-mentioned high values(s).

The OH—:$YO_2$ molar ratio (without correction of trivalent element source) as used in this disclosure does not include correction of acid in the reaction mixture for hydrothermal reaction. It is calculated based on the total mole of hydroxide added to the reaction mixture for hydrothermal reaction divided by the total mole of Y element added to the reaction mixture for hydrothermal reaction. The hydroxide (OH—) source is advantageously alkali metal oxide, e.g., $Li_2O$, $Na_2O$, $K_2O$, $Rb_2O$, $Cs_2O$, $Fr_2O$, or any combination thereof; alkali metal hydroxide, e.g., LiOH, NaOH, KOH, RbOH, CsOH, FrOH, or any combination thereof; ammonium hydroxide, alkali earth metal oxide, e.g., BeO, MgO, CaO, SrO, BaO, RaO, or any combination thereof; alkali earth metal hydroxide, e.g., $Be(OH)2$, $Mg(OH)2$, $Ca(OH)2$, $Sr(OH)2$, $Ba(OH)2$, $Ra(OH)2$, or any combination thereof; oxide(s) or hydroxide(s) of any element selected from Groups 3-17, and any combination thereof; and organic hydroxide(s), such as quarterly ammonium hydroxide(s), hydroxide of organic template (R) used in the synthesis.

The $OH^-:YO_2$ molar ratio (with correction of trivalent element source) as used in this disclosure include correction of acid in the reaction mixture for hydrothermal reaction. The mole of $OH^-$ after correction is calculated by subtracting three times the mole of trivalent element (if the trivalent element source is supplied in the form of salt other than oxide, hydroxide, or metal) from the total mole of hydroxide added to the reaction mixture for hydrothermal reaction. The $OH^-:YO_2$ molar ratio (with correction of trivalent element source) is, therefore, calculated based on the total mole of hydroxide after correction divided by the total mole of Y element added to the reaction mixture for hydrothermal reaction.

In some embodiments of this disclosure, the $OH^-:YO_2$, e.g., $OH^-:SiO_2$ molar ratio ranges from a low value of 0.001, preferably 0.01, and optionally 0.1, to a high value of 2.0, preferably 1, and optionally 0.5. The $OH^-:YO_2$, e.g., $OH^-$:

SiO$_2$ molar ratio ideally falls in a range comprising any combination of the above-mentioned low value(s) and the above-mentioned high values(s).

Directing agent R comprises at least one of N,N,N,N'N'N'-hexamethyl-1,5-pentanediaminium (Me6-diquat-5) salt, e.g., Me6-diquat-5 salt of hydroxide, chloride, bromide, fluoride, nitrate, sulfate, phosphate, or any mixture thereof.

In some embodiment, the directing agent R is selected from the group consisting of Me6-diquat-5 dibromide, Me6-diquat-5 dichloride, Me6-diquat-5 difluoride, Me6-diquat-5 diiodide, Me6-diquat-5 dihydroxide, Me6-diquat-5 sulfate, Me6-diquat-5 dinitrate, Me6-diquat-5 hydroxide bromide, Me6-diquat-5 hydroxide chloride, Me6-diquat-5 hydroxide fluoride, Me6-diquat-5 hydroxide iodide, Me6-diquat-5 hydroxide nitrate, Me6-diquat-5 fluoride bromide, Me6-diquat-5 fluoride chloride, Me6-diquat-5 fluoride iodide, Me6-diquat-5 fluoride nitrate, Me6-diquat-5 chloride bromide, Me6-diquat-5 chloride iodide, Me6-diquat-5 chloride nitrate, Me6-diquat-5 iodide bromide, Me6-diquat-5 bromide nitrate, and any mixtures thereof.

A factor affecting the cost and the product quality of the synthesis of a crystalline molecular sieve is the amount of the directing agent (represented by the R:YO$_2$; e.g., R:SiO$_2$ molar ratio). The directing agent is generally the most expensive reactant(s) in the hydrothermal reaction mixture of many crystalline molecular sieves. The lower the amount of the directing agent in the hydrothermal reaction mixture (low R:YO$_2$; e.g., R:SiO$_2$ molar ratio), the cheaper the final molecular sieve produced.

In some embodiments of this disclosure, the R:YO2; e.g., R:SiO2 molar ratio ranges from a low value of 0.001, preferably 0.05, and optionally 0.1, to a high value of 2.0, preferably 0.5, and optionally 0.15. The R:YO$_2$; e.g., R:SiO$_2$ molar ratio ideally falls in a range comprising any combination of the above-mentioned low value(s) and the above-mentioned high value(s).

It should be realized that the hydrothermal reaction mixture components can be supplied by more than one source. The hydrothermal reaction mixture can be prepared either batchwise or continuously. Crystal size and crystallization time of the crystalline molecular sieve of this disclosure may vary with the nature of the hydrothermal reaction mixture employed and the crystallization conditions.

It will be understood by a person skilled in the art that the synthesis mixture having a composition within the molar ranges as discussed above means that the synthesis mixture is the product of mixing, adding, reacting, or by any means of providing such a mixture, wherein such product has a composition within the molar ranges as discussed above. The product of mixing, adding, reacting, or by any means of providing such a mixture may or may not contain individual ingredients when the synthesis mixture was prepared. The product of mixing, adding, reacting, or by any means of providing such a mixture, may even contain reaction product of individual ingredients when the synthesis mixture was prepared by mixing, adding, reacting, or by any means of providing such a mixture.

Optionally the hydrothermal reaction mixture may contain seed crystals. It is well known that seeding a molecular sieve synthesis mixture frequently has beneficial effects, for example in controlling the particle size of the product, avoiding the need for an organic template, accelerating synthesis, and improving the proportion of product that is of the intended framework type. In some embodiments of this disclosure, the synthesis of the crystalline molecular sieve is facilitated by the presence of 0 to about 25 wt %, preferably about 1 to about 5 wt %, seed crystals based on total weight of tetrahedral element oxide (e.g., silica) of the hydrothermal reaction mixture.

Usually the seeding crystals are from the synthesis similar to the one where they are used. In general any form of the crystalline material may be useful in facilitating synthesis on the new phase.

Crystallization Conditions

Crystallization of the crystalline molecular sieve of this disclosure can be carried out at either static or stirred condition in a reactor vessel, such as for example, autoclaves. The total useful range of temperatures for crystallization is from about 100° C. to about 200° C. for a time sufficient for crystallization to occur at the temperature used, e.g., from about 1 hour to about 400 hours, optionally with agitation of 0-1000 rotation per minutes (RPM). Preferably, the range of temperatures for crystallization is from about 140° C. to about 180° C. for a time sufficient for crystallization to occur at the temperature used, e.g., from about 1 hour to about 200 hours, optionally with agitation of 0-400 RPM.

Thereafter, the crystals are separated from the liquid and recovered. The procedure may include an aging period, either at room temperature (~25° C.) or, preferably, at a moderately elevated temperature, before the hydrothermal treatment ("hydrothermal reaction") at more elevated temperature. The latter may include a period of gradual or stepwise variation in temperature.

Optionally, the hydrothermal reaction is carried out with any type of agitation, e.g., stirring or rotating the vessel about a horizontal axis (tumbling). The rate of the agitation is ranged from 0 to about 1000 RPM, preferably from 0 to about 400 RPM.

In some embodiments, the crystalline molecular sieve of this disclosure is an MCM-22 family material. In some preferred embodiments, the crystalline molecular sieve of this disclosure comprises at least one of MCM-22, MCM-49, MCM-56, an intergrowth-phase of MCM-22, and/or MCM-49, and/or MCM-56, or a mix phase of MCM-22, and/or MCM-49, and/or MCM-56.

The molecular sieve product from the synthesis may further be filtrated, washed with water, and/or dried. The crystalline molecular sieve formed by crystallization may be recovered and subjected for further treatment, such as, ion-exchange with ammonium salt(s) (e.g., ammonium hydroxide, ammonium nitrate, ammonium chloride, ammonium sulfate, ammonium phosphate, or any combination thereof) and/or calcination in an oxidative atmosphere (e.g., air, gas with an oxygen partial pressure of greater than 0 kPa-a) at a temperature of greater than 200° C., preferably at least 300° C., more preferably at least 400° C., and most preferably at least 500° C.

Catalysis and Adsorption

A summary of the molecular sieves and/or zeolites, in terms of production, modification and characterization of molecular sieves, is described in the book "Molecular Sieves-Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known forming techniques, like spray drying, prilling, pelletizing and extrusion, have been and are being used to produce macrostructures in the form of, for example, spherical particles, extrudates, pellets and Tablets of both micropores and other types of porous materials for use in catalysis, adsorption and ion exchange. A summary of these techniques is described in "Catalyst Manufacture," A. B. Stiles and T. A. Koch, Marcel Dekker, N.Y., 1995.

To the extent desired, the original metal cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for certain hydrocarbon conversion reactions. These include hydrogen, rare earth metals and metals of Groups 1-17, preferably Groups 2-12 of the Periodic Table of the Elements.

The crystalline molecular sieve of this disclosure, preferably the MCM-22 family molecular sieve, when employed either as an adsorbent or as a catalyst in an organic compound conversion process should be generally dehydrated, at least partially. This can be done by heating to a temperature in the range of e.g., 200° C. to 595° C. in an atmosphere such as air or nitrogen, and at atmospheric, sub-atmospheric or super-atmospheric pressures for e.g., between 30 minutes and 48 hours. The degree of dehydration is measured by the percentage of weight loss relative to the total weight loss of a molecular sieve sample at 595° C. under flowing dry nitrogen (less than 0.001 kPa partial pressure of water vapor) for 48 hours. Dehydration can also be performed at room temperature (~25° C.) merely by placing the silicate in a vacuum, but a longer time is required to obtain a sufficient amount of dehydration.

When used as a catalyst, the crystalline molecular sieve of this disclosure, preferably the MCM-22 family molecular sieve, should be generally subjected to thermal treatment to remove part or all of any organic constituent. The crystalline molecular sieve of this disclosure, preferably the MCM-22 family molecular sieve, can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be in the composition by way of co-crystallization, exchanged into the composition to the extent a Group 13 element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The above crystalline molecular sieve, preferably the MCM-22 family molecular sieve, especially in its metal, hydrogen and ammonium forms can be beneficially converted to another form by thermal treatment. This thermal treatment is generally performed by heating one of these forms at a temperature of at least 370° C. for at least 1 minute and generally not longer than 1000 hours. While sub-atmospheric pressure can be employed for the thermal treatment, atmospheric pressure is desired for reasons of convenience. The thermal treatment can be performed at a temperature up to about 925° C. The thermal treated product is particularly useful in the catalysis of certain hydrocarbon conversion reactions. The thermally treated product, especially in its metal, hydrogen and ammonium forms, is particularly useful in the catalysis of certain organic, e.g., hydrocarbon, conversion reactions. Non-limiting examples of such reactions include those described in U.S. Pat. Nos. 4,954,325; 4,973,784; 4,992,611; 4,956,514; 4,962,250; 4,982,033; 4,962,257; 4,962,256; 4,992,606; 4,954,663; 4,992,615; 4,983,276; 4,982,040; 4,962,239; 4,968,402; 5,000,839; 5,001,296; 4,986,894; 5,001,295; 5,001,283; 5,012,033; 5,019,670; 5,019,665; 5,019,664; and 5,013,422, each incorporated herein by reference as to the description of the catalytic reactions.

The crystals prepared by the instant invention can be shaped into a wide variety of particle sizes. Generally speaking, the particles can be in the form of a powder, a granule, or a molded product, such as an extrudate. In cases where the catalyst is molded, such as by extrusion, the crystals can be extruded before drying or partially dried and then extruded.

The crystalline molecular sieve(s) of this disclosure, preferably the MCM-22 family molecular sieve(s), may be used as an adsorbent, such as for separating at least one component from a mixture of components in the vapor or liquid phase having differential sorption characteristics with respect to the crystalline molecular sieve(s) of this disclosure. Therefore, at least one component can be partially or substantially totally separated from a mixture of components having differential sorption characteristics with respect to the crystalline molecular sieve(s) of this disclosure by contacting the mixture with the crystalline molecular sieve(s) of this disclosure to selectively sorb the one component.

The crystalline molecular sieve(s) of this disclosure, preferably the MCM-22 family molecular sieve(s) of this disclosure, are useful as catalyst in a wide range of processes, including separation processes and hydrocarbon conversion processes. Specific examples of hydrocarbon conversion processes which are effectively catalyzed by the crystalline molecular sieve(s) of this disclosure, preferably the MCM-22 family molecular sieve(s) of this disclosure, by itself or in combination with one or more other catalytically active substances including other crystalline catalysts, include the following:

(i) alkylation of aromatic hydrocarbons, e.g., benzene, with long chain olefins, e.g., $C_{14}$ olefin, with reaction conditions including, individually or in any combination, a temperature of from about 340° C. to about 500° C., a pressure of from about 101 to about 20200 kPa-a (absolute), a weight hourly space velocity of from about 2 $hr^{-1}$ to about 2000 $hr^{-1}$ and an aromatic hydrocarbon/olefin mole ratio of from about 1/1 to about 20/1, to provide long chain alkyl aromatics which can be subsequently sulfonated to provide synthetic detergents;

(ii) alkylation of aromatic hydrocarbons with gaseous olefins to provide short chain alkyl aromatic compounds, e.g., the alkylation of benzene with propylene to provide cumene, with reaction conditions including, individually or in any combination, a temperature of from about 10° C. to about 125° C., a pressure of from about 101 to about 3030 kPa-a, and an aromatic hydrocarbon weight hourly space velocity (WHSV) of from 5 $hr^{-1}$ to about 50 $hr^{-1}$;

(iii) alkylation of reformate containing substantial quantities of benzene and toluene with fuel gas containing $C_5$ olefins to provide, inter alia, mono- and di-alkylates with reaction conditions including, individually or in any combination, a temperature of from about 315° C. to about 455° C., a pressure of from about 3000 to about 6000 kPa-a, a WHSV-olefin of from about 0.4 $hr^{-1}$ to about 0.8 $hr^{-1}$, a WHSV-reformate of from about 1 $hr^{-1}$ to about 2 $hr^{-1}$ and a gas recycle of from about 1.5 to 2.5 vol/vol fuel gas feed;

(iv) alkylation of aromatic hydrocarbons, e.g., benzene, toluene, xylene and naphthalene, with long chain olefins, e.g., $C_{14}$ olefin, to provide alkylated aromatic lube base stocks with reaction conditions including, individually or in any combination, a temperature of from about 160° C. to about 260° C. and a pressure of from about 2600 to 3500 kPa-a;

(v) alkylation of phenols with olefins or equivalent alcohols to provide long chain alkyl phenols with reaction conditions including, individually or in any combination, a temperature of from about 200° C. to about 250° C., a pressure of from about 1500 to 2300 kPa-a and a total WHSV of from about 2 $hr^{-1}$ to about 10 $hr^{-1}$;

(vi) conversion of light paraffins to olefins and aromatics with reaction conditions including, individually or in any combination, a temperature of from about 425° C. to about 760° C. and a pressure of from about 170 to about 15000 kPa-a;

(vii) conversion of light olefins to gasoline, distillate and lube range hydrocarbons with reaction conditions including, individually or in any combination, a temperature of from about 175° C. to about 375° C. and a pressure of from about 800 to about 15000 kPa-a;

(viii) two-stage hydrocracking for upgrading hydrocarbon streams having initial boiling points above about 260° C. to premium distillate and gasoline boiling range products in a first stage using the MCM-22 family molecular sieve of this disclosure in combination with a Groups 8-10 metal as catalyst with effluent therefrom being reaction in a second stage using zeolite Beta, also in combination with a Groups 8-10 metal, as catalyst, the reaction conditions including, individually or in any combination, a temperature of from about 340° C. to about 455° C., a pressure of from about 3000 to about 18000 kPa-a, a hydrogen circulation of from about 176 to about 1760 liter/liter and a liquid hourly space velocity (LHSV) of from about 0.1 to 10 $h^{-1}$;

(ix) a combination hydrocracking/dewaxing process in the presence of the MCM-22 family molecular sieve of this disclosure and a hydrogenation component as catalyst, or a mixture of such catalyst and zeolite Beta, with reaction conditions including, individually or in any combination, a temperature of from about 350° C. to about 400° C., a pressure of from about 10000 to about 11000 kPa-a, an LHSV of from about 0.4 to about 0.6 and a hydrogen circulation of from about 528 to about 880 liter/liter;

(x) reaction of alcohols with olefins to provide mixed ethers, e.g., the reaction of methanol with isobutene and/or isopentene to provide methyl-t-butyl ether (MTBE) and/or t-amyl methyl ether (TAM) with conversion conditions including, individually or in any combination, a temperature of from about 20° C. to about 200° C., a pressure of from 200 to about 20000 kPa-a, a WHSV (gram-olefin per hour gram-zeolite) of from about 0.1 $hr^{-1}$ to about 200 $hr^{-1}$ and an alcohol to olefin molar feed ratio of from about 0.1/1 to about 5/1;

(xi) toluene disproportionation with $C_9$+ aromatics as co-feed with reaction conditions including, individually or in any combination, a temperature of from about 315° C. to about 595° C., a pressure of from about 101 to about 7200 kPa-a, a hydrogen/hydrocarbon mole ratio of from about 0 (no added hydrogen) to about 10 and a WHSV of from about 0.1 $hr^{-1}$ to about 30 $hr^{-1}$;

(xii) preparation of the pharmaceutically-active compound 2-(4-isobutylphenyl)propionic acid, i.e. ibuprofen, by reacting isobutyl benzene with propylene oxide to provide the intermediate 2-(4-isobutylphenyl)propanol followed by oxidation of the alcohol to the corresponding carboxylic acid;

(xiii) use as an acid-binding agent in the reaction of amines with heterocyclic fiber-reactive components in preparation of dyes to prepare practically salt-free reactive dye-containing solution, as in German Patent No. DE 3,625,693, incorporated entirely herein by reference;

(xiv) as the absorbent for separating 2,6-toluene diisocyanate (2,6-TDI) from isomers if TDI as in U.S. Pat. No. 4,721,807, incorporated entirely herein by reference, whereby a feed mixture comprising 2,6-TDI and 2,4-TDI is contacted with the present MCM-22 family molecular sieve which has been cation-exchanged with K ions to absorb the 2,6-TDI, followed by recovering the 2,6-TDI by desorption with desorbent material comprising toluene;

(xv) as the absorbent for separating 2,4-TDI from its isomers as in U.S. Pat. No. 4,721,806, incorporated entirely herein by reference, whereby a feed mixture comprising 2,4-TDI and 2,6-TDI is contact with the present MCM-22 family molecular sieve which has been cation-exchanged with Na, Ca Li and/or Mg ions to absorb the 2,4-TDI, followed by recovering the 2,4-TDI by desorption with desorbent material comprising toluene; and (xvi) in a process for decreasing the durene content of a 90-200° C.+ bottoms fraction obtained from the catalytic conversion of methanol to gasoline which comprises contacting the durene-containing bottoms fraction with hydrogen over a catalyst of the present MCM-22 family molecular sieve with a hydrogenation metal, at conditions including, individually or in any combination, a temperature of from about 230° C. to about 425° C. and a pressure of from about 457 to about 22000 kPa-a.

In an embodiment, the crystalline molecular sieve(s) of this disclosure, preferably the MCM-22 family molecular sieve(s) of this disclosure, may be used in processes that co-produce phenol and ketones that proceed through benzene alkylation, followed by formation of the alkylbenzene hydroperoxide and cleavage of the alkylbenzene hydroperoxide into phenol and ketone. In such processes, the crystalline molecular sieve(s) of this disclosure, preferably the MCM-22 family molecular sieve(s) of this disclosure, are used in the first step, that is, benzene alkylation. Examples of such processes includes processes in which benzene and propylene are converted to phenol and acetone, benzene and $C_4$ olefins are converted to phenol and methyl ethyl ketone, such as those described for example in international application PCT/EP2005/008557, benzene, propylene and $C_4$ olefins are converted to phenol, acetone and methyl ethyl ketone, which, in this case can be followed by conversion of phenol and acetone to bis-phenol-A as described in international application PCT/EP2005/008554, benzene is converted to phenol and cyclohexanone, or benzene and ethylene are converted to phenol and methyl ethyl ketone, as described for example in PCT/EP2005/008551.

The crystalline molecular sieve(s) of this disclosure, preferably the MCM-22 family molecular sieve(s) of this disclosure, are useful in benzene alkylation reactions where selectivity to the monoalkylbenzene is required. Furthermore, the crystalline molecular sieve(s) of this disclosure, preferably the MCM-22 family molecular sieve(s) of this disclosure, is particularly useful to produce selectively sec-butylbenzene from benzene and $C_4$ olefin feeds that are rich in linear butenes, as described in international application PCT/EP2005/008557. Preferably, this conversion is carried out by co-feeding benzene and the $C_4$ olefin feed with the catalyst of the present invention, at a temperature of about 60° C. to about 260° C., for example of about 100° C. to 200° C., a pressure of 7000 kPa-a or less, and a feed weight hourly space velocity (WHSV) based on $C_4$ alkylating agent of from about 0.1 to 50 $h^{-1}$ and a molar ratio of benzene to $C_4$ alkylating agent from about 1 to about 50.

The crystalline molecular sieve(s) of this disclosure, preferably the MCM-22 family molecular sieve(s) of this disclosure, are also useful catalyst for transalkylations, such as, for example, polyalkylbenzene transalkylations.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e. combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. The materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dictite, narcite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline molecular sieve and inorganic oxide matrix vary widely, with the crystal content ranging from about 1 to about 99 percent by weight and more usually, particularly when the composite is prepared in the form of beads, in the range of about 20 to about 80 wt % of the composite.

These and other facets of the present invention is exemplified by the following Examples.

EXAMPLES

In the Examples, the XRD diffraction patterns of the as-synthesized materials were recorded on a Bruker D4 X-Ray Powder Diffractometer using copper Kα radiation in the 2θ range of 2 to 40 degrees.

The SEM images were obtained on a HITACHI S4800 Field Emission Scanning Electron Microscope (SEM). The crystal size was measured by averaging the size of multiple crystals as shown in the SEM.

The crystallinity is defined as the ratio of the sum of the two main peaks, 7.1 and 26 (2θ), to the ratio of the sum of the same peaks in the standard (reference Example for a given synthesis formulation and conditions), multiplied by 100.

The BET surface area was measured by Micromeritics TriStar 3000 V6.05A (Micromeritics Corporation, Norcross, Ga.) with sample pretreated at 350° C. in air.

The external surface area over overall BET surface area ratio was calculated from the t-plot generated as part of the BET determination by nitrogen sorption.

The following Examples illustrate exemplary preferred embodiments:

Example A

In this example, MCM-22 was prepared according to the method of U.S. Pat. No. 4,954,325.

A hydrothermal reaction mixture was prepared from water, hexamethyleneimine (HMI) (Sigma-Aldrich Company), silica (Ultrasil™, Degussa Corp.), 45 wt % sodium aluminate solution (25.5% Al2O3, 19.5% Na2O; USALCO), and 50 wt % sodium hydroxide solution. The mixture had the following molar composition as shown in Table IX:

TABLE IX

| | Example A |
|---|---|
| Molar composition | |
| $SiO_2/Al_2O_3$ | 30 |
| $H_2O/SiO_2$ | 20 |
| $OH^-/SiO_2$* | 0.17 |
| $Na^+/SiO_2$ | 0.17 |
| $HMI/SiO_2$ | 0.35 |
| Crystallization conditions | |
| Temperature (° C.) | 143 |
| Stirring speed (RPM) | 250 |
| Time (hr) | 72 |
| Characterizations | |
| XRD Result | Pure Phase MCM-22 (FIG. 1) |
| Crystallinity (%) | 100 |
| $SiO_2/Al_2O_3$ (molar ratio) | 23 |
| Total Surface Area ($m^2/g$) | 604 |
| Micropore Surface Area ($m^2/g$) | 506 |
| External Surface Area ($m^2/g$) | 98 |
| Crystal size (SEM) | 0.5 × 0.025 μm plates (FIG. 2) |

*The $OH^-/SiO_2$ of this row is calculated without correction of trivalent element source since aluminum was supplied as $Al_2O_3$.

The hydrothermal reaction mixture was crystallized according to the conditions listed in the Table IX. The XRD of the as-synthesized material of Example A (FIG. 1) showed pure phase MCM-22. The SEM picture of the material of Example A (FIG. 2) showed a platelet morphology with an average crystal size of 0.5×0.025 μm. After calcination, the material exhibited an XRD according to that reported in U.S. Pat. No. 4,954,325.

Examples 1-2

Hydrothermal reaction mixtures were prepared from water, Me6-diquat-5 ("R") dibromide (SACHEM, Inc.), silica (Ultrasil™, Degussa Corp.), aluminum sulfate solution (8.1% $Al_2O_3$) solution, and 50 wt % sodium hydroxide solution. The mixtures had the following molar compositions as shown in Table X:

TABLE X

|  | Example 1 | Example 2 |
|---|---|---|
| Molar composition | | |
| $SiO_2/Al_2O_3$ | 30 | 32 |
| $H_2O/SiO_2$ | 21 | 34 |
| $OH^-/SiO_2$* | 0.28 | 0.47 |
| $Na^+/SiO_2$ | 0.48 | 0.66 |
| $R/SiO_2$ | 0.15 | 0.15 |
| Crystallization conditions | | |
| Temperature (° C.) | 170 | 160 |
| Stirring speed (RPM) | 0 | 0 |
| Time (hr) | 80 | 220 |
| Characterizations | | |
| XRD Result | See FIG. 3 | See FIG. 5 |
| $SiO_2/Al_2O_3$ (molar ratio) | 24 | N/A |
| BET area (m²/g) | 557 | N/A |
| Crystal size (SEM) | >1 μm (FIG. 4) | >1 μm wide (FIG. 6) |
| Platelet Thickness (SEM) | ~0.025 μm (FIG. 4) | ~0.025 μm (FIG. 6) |

*The $OH^-/SiO_2$ of this row is calculated with correction of trivalent element source since aluminum was supplied as aluminum salt.

The mixture of Example 1 was crystallized at 170° C. in a Teflon™ bottle with no stirring for 80 hours. After crystallization, the hydrothermal reaction mixture slurry of Example 1 was filtered. The as-synthesized material had an XRD pattern shown in FIG. 3.

The mixture of Example 2 was crystallized at 160° C. in a Teflon™ bottle with no stirring for 220 hours. After crystallization, the hydrothermal reaction mixture slurry of Example 2 was filtered. The as-synthesized material had an XRD pattern shown in FIG. 5.

The crystalline molecular sieve made in Examples 1 and 2 showed XRD diffractions of pure phase MCM-22 family molecular sieve. The XRD diffraction of the crystalline molecular sieve of Examples 1 and 2 included d-spacing maxima at 13.18±0.25 and 12.33±0.23 Angstroms, wherein the peak intensity of the d-spacing maximum at 13.18±0.25 Angstroms is approximately equal or higher than the peak intensity of the d-spacing maximum at 12.33±0.23 Angstroms. The XRD diffraction of the crystalline molecular sieve of Examples 1 and 2 further included d-spacing maxima at 11.06±0.18 and 9.25±0.13 Angstroms, wherein the peak intensity of the d-spacing maximum at 11.06±0.18 Angstroms is approximately equal or higher than the peak intensity of the d-spacing maximum at 9.25±0.13 Angstroms. Additionally, the d-spacing maxima at 11.06±0.18 and 9.25±0.13 Angstroms were non-discrete peaks.

Further, the XRD diffractions of the crystalline molecular sieve of Examples 1 and 2 were further characterized by including values substantially as shown in Tables II, III, IV, or V.

Example 3

100 grams of 1 M ammonium nitrate solution was mixed with 13 grams of solid from Example 1 (water washed and dried). The mixture was stirred at room temperature (~25° C.) for one hour and filtrated. Another 100 grams of 1 M ammonium nitrate solution was mixed with the filtrated solid from the previous step and stirred at room temperature (~25° C.) for one hour. The mixture was filtered and washed with water. The filtrated and washed solid was dried in an oven for 24 hours at 110° C.

Example 4

The synthesis was carried out in a manner similar to Example 1 except for time of crystallization of 60 hrs. A small sample revealed a fully crystalline product. 400 ml of water was added to the slurry, agitated and supernatant decanted after the solids settled. Water was added again, stirred and the slurry filtered and washed. The final as-synthesized solid product was dried at 121° C. (250° F. ).

15 g of the as-synthesized product was exchanged with ammonium nitrate using 100 g of ammonium nitrate like in Example 4. A portion was calcined in air at 540° C. affording the calcined product with BET surface area of 514 m²/g, external surface area 72 m²/g and the ratio external to total area equal to 0.14.

The X-ray diffraction patterns for the as-synthesized, and ammonium exchanged and calcined materials of Example 4, are shown in FIG. 7.

Example 5

A catalyst was prepared from 80 weight parts of product of Example 1 mixed with 20 weight parts of alumina (LaRoche Versal 300) on a dry basis. The catalyst was slurried in ammonium nitrate, filtered and dried at 120° C. before use. The catalyst was activated by calcining in nitrogen at 540° C., followed by aqueous ammonium nitrate exchange and calcining in air at 540° C.

Example 6

A catalyst was prepared from 80 weight parts of product of Comparative Example A mixed with 20 weight parts of alumina (LaRoche Versal 300) on the dry basis. Water was added to the mixture to allow the resulting catalyst to be formed into extrudates. The prepared extrudates were dried at 120° C. before use. The catalyst was activated by calcining in nitrogen at 540° C., followed by aqueous ammonium nitrate exchange and calcining in air at 540° C.

Example 7

The catalysts prepared in Example 5 and Example 6 were sized to 14/24 mesh and tested for benzene alkylation with propylene. Benzene alkylation with propylene was conducted using the catalysts prepared in Examples 5 and 6. The catalyst was loaded into a catalyst basket into a well-mixed Parr autoclave reactor. Benzene (156.1 grams) and propylene (28.1 grams) were then added in a 3:1 molar ratio of benzene:propylene. The reaction conditions were 130° C. at 2183 kPa-a (300 psig) and the reaction was run for 4 hours. A small sample of product was withdrawn at regular intervals and analyzed using an off-line GC (Model HP 5890). The catalyst performance was assessed by a kinetic activity rate constant based on propylene conversion and selectivity to cumene at 100% propylene conversion.

The activity and selectivity results of Example 5 are shown normalized to the catalyst from Example 6 in the following Table XI.

TABLE XI

| Catalyst | Activity | Selectivity, normalized [DIPB/Cumene (%)] |
|---|---|---|
| Example 6 | 99.6 | 92.1 |
| Example 7 | 100 | 100 |

The catalyst showed both activity and selectivity for the benzene alkylation reaction.

While the illustrative embodiments of this disclosure have been described with particularity, it will be understood that various other modifications will be apparent to and can be readily made by those skilled in the art without departing from the spirit and scope of this disclosure. Accordingly, it is not intended that the scope of the claims appended hereto be limited to the Examples and descriptions set forth herein but rather that the claims be construed as encompassing all the features of patentable novelty which reside in the present invention, including all features which would be treated as equivalents thereof by those skilled in the art to which this disclosure pertains.

We claim:

1. A crystalline molecular sieve having, in its as-synthesized form, an X-ray diffraction pattern including d-spacing maxima at 13.18±0.25 and 12.33±0.23 Angstroms, wherein the peak intensity of said d-spacing maximum at 13.18±0.25 Angstroms is at least as great as 90% of the peak intensity of said d-spacing maximum at 12.33±0.23 Angstroms.

2. The crystalline molecular sieve of claim 1, wherein the peak intensity of the d-spacing maximum at 13.18±0.25 Angstroms is at least as great as the peak intensity of the d-spacing maximum at 12.33±0.23 Angstroms.

3. The crystalline molecular sieve of claim 1, wherein the peak intensity of the d-spacing maximum at 13.18±0.25 Angstroms is at least as great as 110% of the peak intensity of the d-spacing maximum at 12.33±0.23 Angstroms.

4. The crystalline molecular sieve of claim 1, wherein said X-ray diffraction pattern further includes two XRD distinguishable peaks with d-spacing maxima at 11.06±0.18 and 9.25±0.13 Angstroms, wherein the peak intensity of said d-spacing maximum at 11.06±0.18 Angstroms is at least as great as the peak intensity of said d-spacing maximum at 9.25±0.13 Angstroms.

5. The crystalline molecular sieve recited in claim 4, wherein said peaks with d-spacing maxima at 11.06±0.18 and 9.25±0.13 Angstroms are non-discrete peaks.

6. The crystalline molecular sieve recited in claim 5, wherein the X-ray diffraction pattern further includes an XRD distinguishable peak with d-spacing maximum at 9.74±0.15 Angstroms.

7. The crystalline molecular sieve recited in claim 6, wherein the peak with d-spacing maximum at 9.74±0.15 Angstroms is non-discrete peak.

8. The crystalline molecular sieve recited in claim 6, wherein the peak with d-spacing maximum at 9.25±0.13 Angstroms is a shoulder peak.

9. The crystalline molecular sieve recited in claim 1, wherein the X-ray diffraction pattern further includes a d-spacing maximum at 27.42±0.50 Angstroms.

10. The crystalline molecular sieve recited in claim 1, wherein said X-ray diffraction pattern includes values and relative intensity substantially as shown in the following Table:

| Interplanar d-Spacing (Å) | Relative Intensity, $I/I_o \times 100$ |
|---|---|
| 13.18 ± 0.25 | M-VS |
| 12.33 ± 0.23 | M-VS |
| 11.06 ± 0.18 | W-S |
| 9.25 ± 0.13 | W-S. |

11. The crystalline molecular sieve recited in claim 1, wherein said X-ray diffraction pattern includes values and relative intensity substantially as shown in following Table:

| Interplanar d-Spacing (Å) | Relative Intensity, $I/I_o \times 100$ |
|---|---|
| 13.18 ± 0.25 | M-VS |
| 12.33 ± 0.23 | M-VS |
| 11.06 ± 0.18 | W-S |
| 9.25 ± 0.13 | W-S |
| 3.57 ± 0.06 | W-M |
| 3.43 ± 0.06 | M-VS. |

12. The crystalline molecular sieve recited in claim 1, having a total surface area of greater than 450 m$^2$/g as measured by the N$_2$ BET method.

13. The crystalline molecular sieve recited in claim 12, having a ratio of the external surface area over the total surface area of less than 0.15 after conversion into H-form by exchange with ammonium nitrate and calcination, wherein the external surface area is determined from a t-plot of the N$_2$ BET.

14. The crystalline molecular sieve recited in claim 1, having a morphology of tabular habit, wherein at least 50 wt % of said crystalline molecular sieve having a crystal diameter greater than 1 μm as measured by the SEM.

15. The crystalline molecular sieve recited in claim 14, having a morphology of tabular habit, wherein at least 50 wt % of said crystalline molecular sieve having a crystal thickness of about 0.025 μm as measured by the SEM.

16. The crystalline molecular sieve recited in claim 15, having a morphology of tabular habit, wherein at least 50 wt % of said crystalline molecular sieve having a crystal diameter greater than 2 μm as measured by the SEM.

17. The crystalline molecular sieve recited in claim 1 that is an MCM-22 family molecular sieve.

18. A process for hydrocarbon conversion, comprising the step of:
    (a) contacting a hydrocarbon feedstock with said crystalline molecular sieve recited in any one of claims 1-17, under conversion conditions to form a conversion product.

19. A crystalline MCM-22 molecular sieve comprising
    (a) a total surface area of greater than 450 m$^2$/g as measured by the N$_2$ BET method;
    (b) a ratio of the external surface area over the total surface area of less than 0.15 after conversion into H-form by exchange with ammonium nitrate and calcination, wherein the external surface area is determined from a t-plot of the N$_2$ BET; and
    (c) a morphology of tabular habit, wherein at least 50 wt % of the crystalline MCM-22 molecular sieve having a crystal diameter greater than 1 μm as measured by the SEM.

20. A crystalline molecular sieve, said crystalline molecular sieve having, in its as-synthesized form, an X-ray diffraction pattern including d-spacing maxima at 13.18±0.25 and 12.33±0.23 Angstroms, wherein the peak intensity of said d-spacing maximum at 13.18±0.25 Angstroms is at least as great as 90% of the peak intensity of said d-spacing maximum at 12.33±0.23 Angstroms, made by the method comprising the steps of:
    (a) providing a mixture comprising at least one source of at least one tetravalent element (Y), at least one source of at least one alkali or alkali earth metal element, at least one directing-agent (R), water, and optionally at least one source of at least one trivalent element (X), said mixture having the following molar ratio:
    Y:X$_2$=10 to infinity
    H$_2$O:Y=1 to 10000

OH⁻:Y=0.001 to 0.59
M⁺:Y=0.001 to 2
R:Y=0.001 to 2
wherein M is an alkali metal and R is at least one N,N,N,N'N'N'-hexamethyl-1,5-pentanediaminium salt (Me₆-diquat-5 salt(s)), wherein said OH⁻:Y is calculated without trivalent element source correction; and
(b) submitting the mixture at crystallization conditions to form a product comprising the desired crystalline molecular sieve, wherein the crystallization conditions comprise a temperature in the range of from 100° C. to 200° C., and a crystallization time from about 1 hour to 400 hours.

21. The crystalline molecular sieve of claim 20, wherein the H₂O:Y molar ratio is in the range of from about 5 to about 35.

22. The crystalline molecular sieve of claim 20, further comprising OH⁻:Y with trivalent element correction ranges of from 0.01 to 0.39.

23. The crystalline molecular sieve of claim 20, wherein the Y:X₂ is in the range of from 10 to 55.

24. The crystalline molecular sieve of claim 20, wherein the R:Y is in the range of from 0.01 to 0.5.

25. The crystalline molecular sieve of claim 20, wherein the tetravalent element (Y) is silicon.

26. The crystalline molecular sieve of claim 20, wherein the trivalent element (X) is aluminum.

27. A crystalline MCM-22 family molecular sieve, said crystalline MCM-22 family molecular sieve having, in its as-synthesized form, an X-ray diffraction pattern including d-spacing maxima at 13.18±0.25 and 12.33±0.23 Angstroms, wherein the peak intensity of said d-spacing maximum at 13.18±0.25 Angstroms is at least as great as 90% of the peak intensity of said d-spacing maximum at 12.33±0.23 Angstroms, made by the method comprising the steps of:
(a) providing a mixture comprising at least one silicon source (Si), at least one aluminum source (Al), at least one source of at least one alkali or alkali earth metal element, at least one directing-agent (R), and water, said mixture having the following molar ratio:
Si:Al₂=10 to infinity
H₂O:Si=1 to 10000
OH⁻:Si=0.001 to 0.59
M⁺:Si=0.001 to 2
R:Si=0.001 to 2
wherein M is an alkali metal and R is at least one N,N,N,N'N'N'-hexamethyl-1,5-pentanediaminium salt (Me₆-diquat-5 salt(s)), wherein said OH⁻:Si is calculated without trivalent element source correction; and
(b) submitting the mixture at crystallization conditions to form a product comprising the desired crystalline molecular sieve, wherein the crystallization conditions comprise a temperature in the range of from 100° C. to 200° C., and a crystallization time from about 1 hour to 400 hours; and
(c) recovering the crystalline molecular sieve.

28. The crystalline molecular sieve of claim 27, wherein the Si:Al₂ is in the range of from 10 to 55.

29. The crystalline molecular sieve of claim 27, further comprising OH⁻:Y with trivalent element correction ranges of from 0.01 to 0.39.

30. The crystalline molecular sieve of claim 27, wherein the R:Si is in the range of from 0.01 to 0.5.

31. The crystalline molecular sieve of claim 20 or 27, wherein the crystallization conditions further comprise a stirring speed in the range of from 0 to 1000 RPM.

32. The crystalline molecular sieve of claim 20 or 27, wherein the mixture further comprises 0-25 wt % of seed based on the weight of tetravalent element in its oxide form.

33. The crystalline molecular sieve of claim 20 or 27, wherein the R is N,N,N,N'N'N'-hexamethyl-1,5-pentanediaminium dibromide.

34. The crystalline molecular sieve recited in claim 20 or 27, wherein said temperature is in the range of 140 to 180° C.

35. A crystalline molecular sieve, said crystalline molecular sieve having, in its as-synthesized form, an X-ray diffraction pattern including d-spacing maxima at 13.18±0.25 and 12.33±0.23 Angstroms, wherein the peak intensity of said d-spacing maximum at 13.18±0.25 Angstroms is at least as great as 90% of the peak intensity of said d-spacing maximum at 12.33±0.23 Angstroms, made by the method comprising the steps of:
(a) providing a mixture comprising at least one source of at least one tetravalent element (Y), at least one source of at least one alkali or alkali earth metal element, at least one directing-agent (R), water, and optionally at least one source of at least one trivalent element (X), said mixture having the following molar ratio:
Y:X₂=10 to infinity
H₂O:Y=1 to 10000
OH⁻:Y=0.74 to 2
M⁺:Y=0.001 to 2
R:Y=0.001 to 2
wherein M is an alkali metal and R is at least one N,N,N,N'N'N'-hexamethyl-1,5-pentanediaminium salt (Me₆-diquat-5 salt(s)), wherein said OH⁻:Y is calculated without trivalent element source correction; and
(b) submitting the mixture at crystallization conditions to form a product comprising the desired crystalline molecular sieve, wherein the crystallization conditions comprise a temperature in the range of from 100 ° C. to 200° C., and a crystallization time from about 1 hour to 400 hours; and
(c) recovering the crystalline molecular sieve.

36. The crystalline molecular sieve of claim 35, wherein the H₂O:Y molar ratio is in the range of from about 5 to 35.

37. The crystalline molecular sieve of claim 35, further comprising OH⁻:Y with trivalent element correction ranges of from 0.64 to 2.

38. A crystalline molecular sieve, said crystalline molecular sieve having, in its as-synthesized form, an X-ray diffraction pattern including d-spacing maxima at 13.18±0.25 and 12.33±0.23 Angstroms, wherein the peak intensity of said d-spacing maximum at 13.18±0.25 Angstroms is at least as great as 90% of the peak intensity of said d-spacing maximum at 12.33±0.23 Angstroms, made by the method comprising the steps of:
(a) providing a mixture comprising at least one source of at least one tetravalent element (Y), at least one source of at least one alkali or alkali earth metal element, at least one directing-agent (R), water, and optionally at least one source of at least one trivalent element (X), said mixture having the following molar ratio:
Y:X₂=10 to infinity
H₂O:Y=5 to 35
OH⁻:Y=0.001 to 2
M⁺:Y=0.001 to 2
R:Y=0.001 to 2
wherein M is an alkali metal and R is at least one N,N,N,N'N'N'-hexamethyl-1,5-pentanediaminium salt (Me₆-diquat-5 salt(s)), wherein said OH⁻:Y is calculated with or without trivalent element source correction; and (b) submitting the mixture at crystallization conditions to form a product comprising the desired crystalline molecular sieve, wherein the crystallization conditions comprise a temperature in the range of from 100° C. to 200° C., and a crystallization time from about 1 hour to 400 hours; and (c) recovering the crystalline molecular sieve.

39. The crystalline molecular sieve of claim 38, wherein the OH⁻:Y is in the range of from 0.01 to 0.5.

40. The crystalline molecular sieve of claim 35 or 38, wherein the Y:$X_2$ is in the range of from 10 to 55.

41. The crystalline molecular sieve of claim 35 or 38, wherein the R:Y is in the range of from 0.01 to 0.5.

42. The crystalline molecular sieve of claim 35 or 38, wherein the tetravalent element (Y) is silicon.

43. The crystalline molecular sieve of claim 35 or 38, wherein the trivalent element (X) is aluminum.

44. The crystalline molecular sieve of claim 35 or 38, wherein the crystallization conditions further comprise a stirring speed in the range of from 0 to 1000 RPM.

45. The crystalline molecular sieve of claim 35 or 38, wherein the mixture further comprises 0-25 wt % of seed based on the weight of tetravalent element in its oxide form.

46. The crystalline molecular sieve of claim 35 or 38, wherein the R is N,N,N,N'N'N'-hexamethyl-1,5-pentanediaminium dibromide.

47. The crystalline molecular sieve recited in claim 35 or 38, wherein said temperature is in the range of 140 to 180° C.

* * * * *